US005696087A

United States Patent [19]
Tang et al.

[11] Patent Number: 5,696,087
[45] Date of Patent: Dec. 9, 1997

[54] METHOD AND COMPOSITIONS FOR REDUCING CHOLESTEROL ABSORPTION

[75] Inventors: Jordan J. N. Tang, Edmond; Chi-Sun Wang, Oklahoma City, both of Okla.

[73] Assignee: Oklahoma Medical Research Foundation, Oklahoma City, Okla.

[21] Appl. No.: 347,718

[22] Filed: Dec. 1, 1994

[51] Int. Cl.$^6$ .................. A61K 38/16; A61K 38/08; A61K 38/10

[52] U.S. Cl. .................. 514/12; 514/13; 514/14; 514/15; 514/16; 514/17; 514/18

[58] Field of Search .................. 514/12, 13, 14, 514/15, 16, 17, 18, 10

[56] References Cited

U.S. PATENT DOCUMENTS

| | | | |
|---|---|---|---|
| Re. 33,885 | 4/1992 | Mattson | 514/23 |
| 4,602,003 | 7/1986 | Maginow | 514/26 |
| 4,944,944 | 7/1990 | Tang et al. | |
| 4,976,968 | 12/1990 | Steiner | |
| 5,017,565 | 5/1991 | Lange, III et al. | |
| 5,063,210 | 11/1991 | Lange, III et al. | |
| 5,173,408 | 12/1992 | Lange, III et al. | |
| 5,200,183 | 4/1993 | Tang et al. | |
| 5,376,640 | 12/1994 | Miyazaki et al. | 514/12 |
| 5,519,001 | 5/1996 | Kushwaha et al. | 514/12 |

FOREIGN PATENT DOCUMENTS

| | | |
|---|---|---|
| 0 333 523 | 9/1989 | European Pat. Off. |
| WO 89/08465 | 9/1989 | WIPO |
| WO 91/06286 | 5/1991 | WIPO |
| WO 91/06287 | 5/1991 | WIPO |
| 9115234 | 10/1991 | WIPO |
| 9420610 | 9/1994 | WIPO |

OTHER PUBLICATIONS

Nilsson et al "Eur. J. Biochem" vol. 192 pp. 543–550 (1990).
Baba et al "Biochem" 1991 vol. 30 pp. 500–510.
Wang and Johnson, "Purification of Human Milk Bile Salt-Acticated Lipase," Anal. Biochem. 133:457–461 (1983).
Wang, C.-S., "Human Milk Bile Salt–activated Lipase", J. Biol. Chem. 256:10198–10202 (1981).
Wang, "Acyl–chain specificity of human milk bile–salt–activated lipase," Biochem. J. 279:297–302 (1991).
Wang, C.-S., and R.L. Smith, "Lowry Determination of Protein in the Presence of Triton X–100", Anal. Biochem. 63:414–417 (1975).
Wang, et al., "Bile Salt–Activated Lipase Mediates Cholesterol Absorption by Binding of its Mucin–Like Region to Intestinal Surface," Science (1995)*.
Wang, et al., "Bile–salt–activated lipase: effect on kitten growth rate," Am. J. Clin. Nutr. 49:457–463 (1989).
Wang, "Purification of Carboxyl Ester Lipase from Human Pancrease and the Amino Acid Sequence of the N–Terminal Region," Biochem. and Biophys. Res. Comm. 155:950 (1988).
Westphal, H., "Transgenic mammals and biotechnology," FASEB J. 3:117–120 (1989).

"CV Therapeutics Begins Phase I Trial on Cholesterol–Reduction Agent," Biotech. Bulletin p. 11 (1994).
Lopez–Candales, et al., "Cholesterol Transport Function of Pancreatic Cholesterol Esterase: Directed Sterol Uptake and Esterification in Enterocytes," Biochem. 32:12085–12089 (1993).
Lowry, O.H., et al., "Protein Measurement with the Folin Phenol Reagent," J. Biol. Chem. 193:265 (1951).
Luckow, V.A. and Summers, M.D., "Trends in the Development of Baculovirus Expression Vectors", Bio/Technology 6:47 (1988).
McKean, et al., "Effects of Inhibitors of Pancreatic Cholesterol Ester Hydrolase (PCEH) On $^{14}$C–cholesterol Absorption in Animal Models," FASEB Journal 6(4):PA1388 (1992).
Nilsson, J., et al., "cDNA cloning of human–milk bile–salt–stimulated lipase and evidence for its identity to pancreatic carboxylic ester hydrolase," Eur. J. Biochem. 192:543–550 (1990).
Nilsson–Ehle, P., and M.C. Schotz, J. Lipid Res. 17:536–541 (1976)*.
Poorman, et al., "Isolation and Characterization of Native Human Renin Derived from Chinese Hamster Ovary Cells," Proteins 1:139–145 (1986).
Reue, K., et al., "cDNA cloning of carboxyl ester lipase from human pancrease reveals a unique proline–rich repeat unit," J. Lipid Res. 32:267–276 (1991).
Rudd, Edwin A., "Pancreatic carboxyl ester," Lipases (Elsevier, publishers, 1984).
Scahill, S.J., et al., "Expression and characterization of the product of a human immune interferon cDNA gene in Chinese hamster ovary cells," Proc. Natl. Acad. Sci., U.S.A. 80:4654–4658 (1983).
Segel, I.H., "Enzyme Activation," Enzyme Kinetics 227–231, John Wiley & Sons, New York (1975).
Studier, F.W. et al., "Use of T7 RNA Polymerase to Direct Expression of Cloned Genes," Methods Enzymol. 185:60–89 (1990).
Wang, et al., "Kinetics of Acylglycerol Sequential Hydrolysis by Human Milk Bile Salt Activated Lipase and Effect of Taurocholate as Fatty Acid Acceptor," Biochem. 27:4834 (1988).
Wang & Kloer, "Kinetic Properties of Human Pancreatic Carboxylesterase," Biochim. et Biophys. Acta 754:142–149 (1983).
Wang, C.-S., and J.A. Hartsuck, "Bile salt–activated lipase. A multiple function lipolytic enzyme," Biochim. Biophys. Acta 1166:1–19 (1993).

(List continued on next page.)

Primary Examiner—Herbert J. Lilling
Attorney, Agent, or Firm—Arnall Golden & Gregory, LLP

[57] ABSTRACT

Compositions including all or a portion and chemically or recombinantly synthesized analogues of the carboxy terminal region of bile salt-activated lipase (BAL) are described, which, when orally ingested, compete with native BAL in binding to the intestinal surface and thus reduce the amount of cholesterol taken into the blood stream.

6 Claims, 3 Drawing Sheets

OTHER PUBLICATIONS

Freed, et al., "Bile salt–stimulated lipase in non–primate milk: longitudinal variation and lipase characteristics in cat and dog milk," *Biochim. and Biophy. Acta* 878:209–215 (1986).

Gallo, et al., "Inhibition of Cholesterol Absorption in Rat Intestine with a Specific Cholesterol Esterase Inhibitor," *FASEB Journal* 6(4): PA1388 (1992).

Ganong, W.F., *Review of Medical Physiology* 249–250 (Lang Medical Publications, 1985)*

Gray, et al., "Primary structure of Mucor miehei aspartyl protease: evidence for a zymogen intermediate," *Gene* 48:41–53 (1987).

Griggs, et al., "Identification and Quantitation of Alditol Acetates of Neutral and Amino Sugars from Mucins by Automated Gas–Liquid Chromatography," *Anal. Biochem.* 43:369–381 (1971).

Hall and Muller, "Studies on the Bile Salt Stimulated Lipolytic Activity of Human Milk Using Whole Milk as Source of Both Substrate and Enzyme," *Pediatr. Res.* 16:251–255 (1982).

Hernell and Blackberg, "Bile–Salt–Stimulated Lipase of Human Milk and Lipid Digestion in the Neonatal Period," *J. Pediatr. Gastro. and Nutri.* 2(Suppl. 1):S242–S247 (1983).

Hewick, R.M., et al., "A Gas–Liquid Solid Phase Peptide and Protein Sequenator," *J. Biol. Chem.* 256:7990–7997 (1981).

Huang and Hui, "Metabolic fate of pancrease–derived cholesterol esterase in intestine: an in vitro study using Caco–2 cells," *J. of Lipid Res.* 31:2029 (1990).

Hui, D.Y., and J.A. Kissel, "Sequence identify between human pancreatic cholesterol esterase and bile salt–stimulated milk lipase," *FEBS Lett.* 276:131–134 (1990).

Innis, M.A., and D.H. Gelfand, in *PCR Protocols. A Guide to Methods and Application* 3–12, Innis, M.A., et al. (Eds.), Academic Press, New York, N.Y. (1990)*.

Jaenisch, R., "Transgenic Animals," *Science* 240:1468–1474 (1988).

Klag, M.J., et al., "Serum Cholesterol in Young Men and Subsequent Cardiovascular Disease," *New Eng. J. Med.*, 328 (5), pp. 313–318 (Feb. 4, 1993).

Kraft, et al., "Using Mini–Prep Plasmid DNA for Sequencing Double Stranded Templates with Sequenase," *BioTechniques* 6:544–547 (1988).

Leary, W.e., "Survey Finds Major Gains in Cutting Blood Cholesterol," *New York Times*, section A, p. 18, col. 3 (Jun. 16, 1993).

Bierman, E.L., "Disorders of the Vascular System: Atherosclerosis and Other Forms of Arteriosclerosis," in *Harrison's Principles of Internal Medicine* 1014–1024, (E. Braunwald et al. 1987).

Bitter, G.A. et al., "Expression and Secretion Vectors for Yeast," *Methods in Enzymology* (Wu and Grossman, eds.) 153:516–544.

Bosner, et al., "Assessment of percent cholesterol absorption in humans with stable isotopes," *J. of Lipid Res.* 34:1047 (1993).

Bosner, et al., "Receptor–like function of heparin in the binding and uptate of neutal lipids," *Proc. Natl. Acad. Sci. USA* 85:7438–7442 (1988).

Bremel, R.D., Yom, H.C. and Bleck, G.T. *J. Dairy Sci.* 72:2826–2833 (1989)*

Brodt–Eppley and Hui, "Dietary regulation of cholesterol esterase mRNA level in rat pancreas," *J. of Lipid Res.* 35:27 (1994).

Brown, M.S., and J.L. Goldstein, "The Hyperlipoproteinemias and Other Disorders of Lipid Metabolism," in *Harrison's Principles of Internal Medicine* 1650–1661.

Clare, J.J. et al., "High–Level Expression of Tetanus Toxin Fragment in Pichia Pastoris Strains Containing Multiple Tanden Integrations of the Gene," *Bio/Technology* 9:455–460 (1991).

Clark, et al., "Inhibition of Hypercholesterolemia (Hyper C) by Specific Pancreatic Cholesterol Ester Hydrolase (PCEH) Inhibitors," *FASEB J.* 6"PA1388 (1992).

Cullen, D. et al., "Controlled Expression and Secretion of Bovine Chymosin in Aspergillus Nidulans," *Bio/Technology* 5:369–378 (1987).

Cullen, D., Gray, G.L., and Berka, R.M., Molecular Cloning Vectors for Aspergillus and Neurospora, in *A Survey of Molecular Cloning Vectors and their Uses*, (Butterworth Publishers, Stoneham, MA (1986)*

DiPersio, et al., "Purification of Pancreatic Cholesterol Esterase Expressed in Recombinant Baculovirus–Infected Sf9 Cells," *Protein Expr. Purif.* 3:114–120 (1992).

Downs, D. et al., "Proline–rich domain and glycosylation are not essential for the enzymic activity of bile salt–activated lipase. Kinae studies of a truncated form of the enzyme (T–BAL) expressed in *E. coli*," *Biochemistry* 33:7980–7985 (1994).

Dubois, et al., "Colorimetric Method for Determination of Sugars and Related Substances," *Anal. Chem.* 28:350–356 (1956).

Elhammer, A.P. et al., "The Specificity of UDP–GalNAc: Polypeptide N–Acetylgalactosaminyltransferase as Inferred from a Database of in Vivo Substrates and from the in Vitro Glycosylation of Proteins and Peptides," *J. Biol. Chem.* 268:10029–10038 (1993).

Baba, T. et al., "Structure of Human Milk Bile Salt Activated Lipase," *Biochemistry* 30:500–510 (1991).

Barr, et al., "Protocol for Efficient Secretion of HSA Developed from *Pichia pastoris*," *Pharmaceutical Engineering* 12:48–51 (1992).

Bevington, P.R., in *Data Reduction and Error Analysis for the Physical Sciences* 56–65 and 204–246, McGraw–Hill, New York (1969)*.

METHOD AND COMPOSITIONS FOR REDUCING CHOLESTEROL ABSORPTION

The U.S. government has certain rights in this invention by virtue of research grant HD-23472 from the National Institutes of Health.

BACKGROUND OF THE INVENTION

The present invention is in the field of dietary science and more particularly relates to the use of bile salt-activated lipase to reduce cholesterol uptake in the intestine.
Cardiovascular and Other Diseases Associated with High Cholesterol Hyperlipidemias, particularly hypercholesterolemia and the hyperlipoproteinemias, are among the most potent risk factors in the causation of atherosclerosis. Hyperlipoproteinemias are also implicated in the development of pancreatitis. A long-established theory suggests that the higher the circulating levels of cholesterol, usually in the form of low density lipoproteins (LDLs) containing cholesterol, the more likely it is to gain entrance to the arterial wall and cause atherosclerosis. (M. S. Brown and J. L. Goldstein, "The Hyperlipoproteinemias and Other Disorders of Lipid Metabolism," in *Harrison's Principles of Internal Medicine* 1650–1661 (E. Braunwald et al. 1987)).

Cardiovascular disease is the leading cause of death in women and middle-aged American men. In 1988, more than 41,000 U.S. residents died of cardiovascular disease before the age of 50. Atherosclerosis, however, which is known to contribute to cardiovascular disease and stroke, begins at a much earlier age. Fatty streaks are common in the arterial walls of children, and a high prevalence of coronary-artery lesions has been found in young men who die accidentally or violently. Children and adolescents with elevated serum cholesterol levels are more likely than their counterparts with normal cholesterol levels to have parents with coronary heart disease. Higher serum cholesterol levels in childhood have been associated with aortic atherosclerosis at autopsy in adolescents and young adults, and both aortic and coronary atherosclerosis in men ranging from 15 to 34 years of age have been correlated with postmortem cholesterol levels. Klag, M. J., et al., *New Eng. J. Med.*, 328(5), pp.313–318 (Feb. 4, 1993).

Cholesterol is used by the body in the synthesis of the steroid hormones by certain endocrine glands and of bile acids by hepatocytes, and is an essential constituent of cell membranes. It is found only in animals. Related sterols occur in plants, but plant sterols are not absorbed from the gastrointestinal tract. Most of the dietary cholesterol is contained in egg yolks and animal fat.

Cholesterol that is taken up in the intestine is derived directly from the diet and from cholesterol-containing bile salt and acids and free cholesterol synthesized in the liver and secreted into the intestine via bile ducts. Cholesterol esters from the bile and diet are absorbed from the lumen of the small intestine by the intestinal epithelial lining cells and incorporated intracellularly into chylomicrons and, in minor amounts, incorporated into very low density lipoproteins (VLDLs), both of which are secreted into lymphatics that ultimately join the bloodstream. The chylomicrons and VLDLs deliver their triacyglycerols and some of their cholesterol to cells in endothelial, muscle, and adipose tissue. The cholesterol-enriched chylomicron remnants and VLDLs then deliver cholesterol back to the hepatocytee and to other cells of the vascular wall along the way. W. F. Ganong, *Review of Medical Physiology* 249–250 (Lange Medical Publications, 1985). The VLDLs from intestinal and liver cells can be converted to low density lipoproteins (LDLs) by discharge of their triacylglycdrols. LDLs contain three-fourths of the total plasma cholesterol.

In hypercholesterolemia, the increase in the blood cholesterol level is associated mainly with a rise in LDL concentrations. However, the specific causes of hypercholesterolemia are complicated and varied. At least one kind of hypercholesterolemia is caused by a mutation in the gene for the LDL receptor that moves cholesterol out of the blood, primarily in the liver. Much more commonly, hypercholesterolemia has been associated with high dietary cholesterol, resulting in high cholesterol uptake from the intestine into the circulating blood.

Reduction of hypercholesterolemia results in a delayed onset of atherosclerosis and a decrease in progression of atherosclerosis, thus reducing the risk of coronary heart disease in humans and other primates. Specifically, there is evidence in animals, most notably primates, that relatively complicated plaques induced by hyperlipidemia will regress, and that further progression of atherosclerosis will cease when hyperlipidemia is removed. Therefore, efforts to prevent atherogenesis, to interrupt progression, and perhaps to promote regression of existing lesions by risk factor reduction are warranted. E. L. Bierman, "Disorders of the Vascular System: Atherosclerosis and Other Forms of Arteriosclerosis," in *Harrison's Principles of Internal Medicine* 1014–1024, (E. Braunwald et al. 1987).

Some forms of hyperlipidemia, including hypercholesterolemia, are potentially partially reversible with current techniques of preventive management. However, none of the current techniques is completely successful and many are associated with unwanted side effects and complications. Taking cholesterol-lowering drugs can result in a twenty percent reduction in serum cholesterol. However, drugs are not always warranted for hypercholesterolemia, and some of the hypolipemic drugs, such as Lovastatin, mevastatin, cholestyramine (Questran), Clofibrate, Probucol, and nicotinic acid, may have serious side effects, including an increase in mortality through liver complications, or less severe side effects, such as constipation (cholestyramine), skin flushes, and muscle dysfunction. W. E. Leafy, *New York Times*, section A, page 18, column 3 (Jun. 16, 1993) or may have an effect in lowering blood triacylglycerol but not cholesterol. Dietary therapy is usually recommended for all patients with hypercholesterolemia but is not always effective.

Accordingly, there is a need for methods and compositions which are effective in lowering blood lipid levels, especially cholesterol levels, especially those that do not in themselves have significant side effects, and in treating disease states associated with high levels of blood lipids, especially in those persons at high risk of heart disease, or who have already suffered heart attacks.

It is therefore an object of the present invention to provide compositions and methods of use in lowering serum cholesterol in a patient in need thereof.

SUMMARY OF THE INVENTION

Compositions including all or a portion of the carboxy terminal region of human bile salt-activated lipase (BAL) are described, which, when orally ingested, compete with native BAL in binding to the intestinal surface, thus reducing the physiological role of BAL in mediating the transfer of cholesterol into the intestinal cells, and, as a result, reducing the amount of cholesterol absorbed from the intestine into the blood stream. The carboxy terminal region of BAL (C-tail), includes amino acid residues 539 to 722, and has a mucin-like structure containing sixteen repeating proline-rich units of eleven amino acid residues each, most having the consensus sequence of PVPPTGDSGAP (SEQ ID NO. 6).

DETAILED DESCRIPTION OF THE INVENTION

Compositions including all or a portion of the carboxy terminal region ("C-tail") of bile salt-activated lipase (BAL), or functional equivalents thereof, are described, which, in the intestine, compete with native BAL in binding to the intestinal surface to reduce the function of endogenous BAL to mediate the uptake of cholesterol eaters or free cholesterol in the form of free cholesterol taken into the blood stream.

Bile Salt-activated Lipase

Warm-blooded animals synthesize many forms of lipases of different structures and activities, which are secreted by mammary gland cells and by cells in several of the digestive organs, including the pancreas, stomach, and small intestine. Bile salt-activated lipase (BAL), which is virtually inactive by itself toward physiological substrates, is activated in the intestine by bile salts. BALs are synthesized and secreted by the pancreas and also by the mammary glands of only few species, including humans, gorillas, cats, and dogs. The amino acid and cDNA sequences of human milk BAL are the same as those of pancreatic BAL, also known as pancreatic carboxylesterase, and closely related to or the same as lipases referred to in the literature as lysophospholipase, cholesterol esterase, sterol ester hydrolase, non-specific lipase, lipase A, carboxyl ester lipase, and cholesterol ester hydrolase, with certain species differences. (Wang, C.-S., and J. A. Hartsuck, "Bile salt-activated lipase. A multiple function lipolytic enzyme," 1166 *Biochem. Biophys. Acta* 1–19 (1993)). Pancreatic BAL is distinct from other types of lipases: pancreatic lipase and phospholipase.

In the intestinal lumen, BAL becomes attached to the intestinal surfaces, most likely the surface of intestinal epithelial lining cells. It can be released from the lumenal surface by EGTA, galactose and fucose, but not by heparin, isotonic buffer, or sodium chloride as demonstrated below. BAL, in the required presence of bile salts, is essential for hydrolyzing cholesterol esters to free cholesterol or to bind free cholesterol in the food. Both of these processes are necessary to allow the uptake of cholesterol since it is the only known pancreatic lipolytic enzyme that can mediate cholesterol uptake. BAL also hydrolyzes carboxyl ester bonds of acylglycerols, phospholipid, and vitamin esters, forming fatty acids and glycerol, and can act on emulsified, micellar, or soluble substrates. It is thought that bile salt causes conformational change in BAL to provide active site access for the bulky substrate molecule and provides additional lipid binding capability in forming the enzyme-substrate complex. Additionally, it is thought that bile salt acts as a fatty acid acceptor during BAL catalysis.

Figure 1:
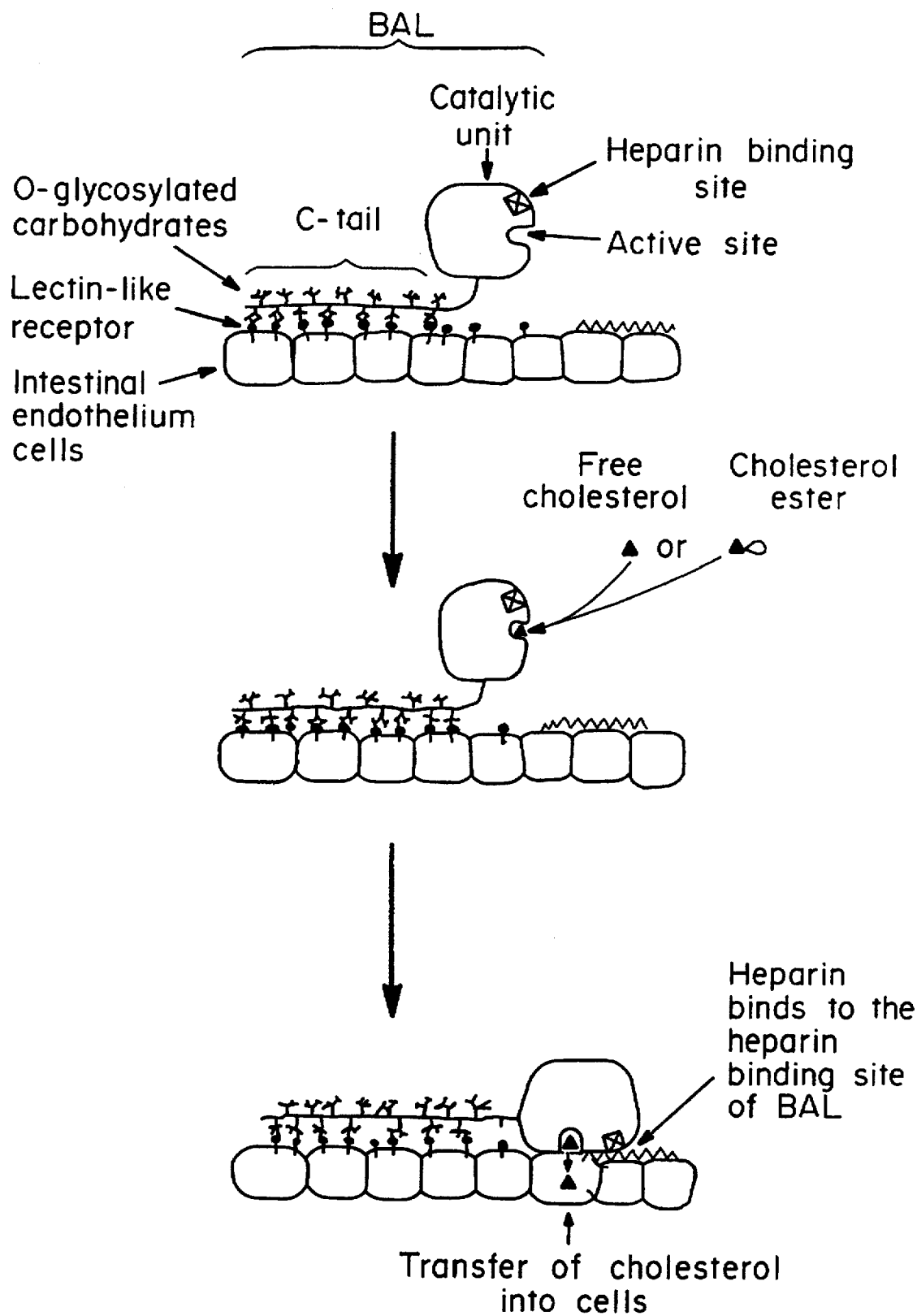
FIG. 1 shows the proposed binding of BAL to intestinal endothelium cells via the C-tail O-glycosylated carbohydrate binding to a lectin-like receptor, binding of cholesterol and cholesterol ester to BAL, hydrolyzing cholesterol ester by BAL, followed by transfer of enzyme bound cholesterol into cells.

The proposed mechanism for the action of BAL is shown in FIG. 1. BAL binds via the C-tail O-glycosylated carbohydrates to a lectin-like receptor on the surface of intestinal endothelium cells. The catalytic unit of the enzyme remains away from the endothelium cells, with the heparin binding site and active site exposed. Free cholesterol or cholesterol ester is then bound to the active site, and, in the case of cholesterol ester, hydrolyzes it to free cholesterol. The catalytic unit then binds to the heparin on the cell surface and transfers the cholesterol into the cells.

Cholesterol, fatty acids, and monoacyglycerols derived from lipolysis by BAL in the intestinal lumen are taken up by the intestinal epithelial lining cell (mucosal cell), where those are reesterified to intracellular triacylglycerols. Cholesterol interacts in the cell with these reesterified triacylglycerols plus apolipoproteins and phospholipid to form chylomicrons and very low density lipoproteins, which are secreted into the lymphatics that ultimately join the blood vascular system for systemic circulation.

The Carboxy Terminal Region of the BAL Molecule

The full, mature, human BAL contains 722 amino acid residues (Sequence ID No. 1). The carboxy terminal region (C-tail) refers to a region including residues 539 to 722. The C-tail of the human BAL molecule has many O-linked oligosaccharide units which form a mucin-like structure. The amino acid sequence of the C-tail contains sixteen repeating proline-rich units of eleven amino acid residues each, most having the consensus sequence of PVPPTGDSGAP (Sequence ID No. 6) (Baba et al., Biochemistry 30:500–510, 1991). By performing the beta-elimination reaction, the C-tail was determined to be O-glycosylated primarily at threonine and, to a small degree, if any, at one serine residue. It is believed that the serine residue, which has an adjacent aspartic acid, is not favorable for the O-glycosylation (Elhammer, A. P. et.al. *J.Biol.Chem.* 268:10029–10038, 1993). A peptide prepared by cyanogen bromide digestion of the C-tail was found to contain most of the carbohydrate of the native BAL (Baba et al., 1991).

As demonstrated below, T-BAL, which does not include the C-tail binding portion, is ineffective in transferring cholesterol into intestinal cells since the enzyme is not bound to the intestinal surface; similarly, C-tail itself can bind to the intestinal surface, and in fact, can compete with native BAL for this binding, but cannot transfer cholesterol since the catalytic unit is either not functional or not present.

As used herein, "C-tail" refers to any part of the carboxy terminal region of BAL as defined above, which is capable of binding to intestinal endothelium cells and inhibiting the binding of native BAL. This can be achieved through the use of BAL consisting of all or part of the mucin-like C-tail region. The rat pancreatic esterase C-tail has only four repeating units and is an example of a C-tail consisting of fewer repeating units than native human BAL. However, it binds to rat intestine surface. It is expected that even shorter tails would also bind to intestinal surface, although with a lower affinity. The tail may be O-glycosylated to different extents with respect to the number of threonine and serine residues, and can include amino acid deletions, substitutions, or additions which do not significantly impair binding to the intestinal surface. The substitutions, deletions, or additions which do not alter binding are readily determined by a screening assay, in which the protein is allowed to bind to intestinal surface, then removed by washing with buffer with increasing concentrations of salt. An example of a BAL which contains a deletion not affecting binding of the C-tail is a BAL lacking the heparin binding site, which is postulated to be present between amino acid residues 56 and 62 (Baba et al., 1991).

Full length BAL which has an inactivated catalytic site can also be used for competitive inhibition of binding of cholesterol. Since the catalytic site is inactivated, the BAL cannot facilitate uptake of choloesterol. The catalytic site can be inactivated by amino acid deletion or substitution in the active site of the recombinant BAL. The catalytic site can also be inactivated by chemical modification of BAL at or near the active site, for example, by proteolysis or other enzymic reactions, by binding of an irreversible enzyme inhibitor to the catalytic site, or by means which disrupt the three dimensional conformation of the catalytic unit of BAL (since the binding of the mucin-like C-tail to intestine is not dependent on its conformation). Examples of disruptive means include detergents and heat.

There are several ways to make a BAL C-tail. For example, one may obtain natural or recombinant BAL and cleave off the C-tail using proteases, such as trypsin, chymotrypsin, pepsin and others, or chemical methods such as cyanogen bromide cleavage at Met-X bonds. Alternatively, one can express in an eukaryotic host the gene or cDNA encoding the sequence including the C-tail region of BAL either by itself or as fusion to other non-BAL DNA sequences which may facilitate either the expression or the purification of recombinant C-tail. The recombinant BAL or C-tail fusions can be subjected to cleavages and purification to obtain purified C-tail.

BAL can be purified from natural sources, such as the milk of human and certain species or animal intestines or pancreatic juice, although this is impractical on a large scale. It is preferably produced by genetic engineering using standard recombinant DNA technology and eukaryotic host cells, such as yeast or cultured mammalian or insect cells, so the C-tail can be properly glycosylated, or in the milk of transgenic non-human animals.

One method of isolating BAL from milk is described by Wang and Johnson, Anal. Biochem. 133:457–461 (1983), incorporated herein by reference.

To synthesize recombinant BAL containing the C-tail or the C-tail itself, one may utilize the cDNA sequence encoding human milk bile salt activated lipase (Sequence ID No. 3) set out in U.S. Pat. No. 5,200,183 to J. J. N. Tang, and C.-S. Wang; Baba, T, et al., Biochemistry 30:500–510 (1991); or Nilsson, J., et al., Eur. J. Biochem. 192:543–550 (1990), all incorporated herein by reference. This can be readily adapted for expression of a protein containing the C-tail, either by deletion, addition, or substitution of the sequence encoding native BAL, as described above.

Since in many eukaryotic expression systems exons are excised correctly, both human BAL cDNA and human BAL genomic DNA can be used to direct the synthesis of recombinant human BAL protein(s) in native or modified forms. Human BAL gene(s) are expected to contain in their untranslated region sequences which regulate the expression of the enzyme. These regulatory sequences may even be directly used in the transgenic animal expression.

Recombinant BAL protein can be produced from human BAL cDNA or genes by many different methods. These include the expression of BAL in hosts such as E. coli, Bacillus, yeast, fungi, insect cells, mammalian cells, and transgenic animals. Expression of T-BAL (truncated form of BAL without C-tail) in E. coli has been described by Downs, D. et al., Biochemistry 33:7980–7985, 1994. Since prokaryotic hosts cannot excise mammalian introns from mRNA, it is preferable to express the cDNA, with appropriate modifications, in procaryotic systems, rather than the gene. However, since procaryotes cannot glycosylate BAL, it is preferable to use eucaryotic systems for expression of BAL. When eukaryotic cells are used as hosts, either human BAL genes or cDNA can be used to direct the synthesis of the enzyme. There can also be glycosylation on BAL provided that a 'leader' or 'signal' sequence is present to direct newly synthesized BAL to the inside of the rough endoplasmic reticulum. This is important for the C-tail to reduce cholesterol uptake since the interaction of intestinal surface is through the oligosaccharides on the C-tail.

In all cases, the human BAL cDNA or gene can be inserted into appropriate expression vectors containing expression regulatory elements, such as transcription initiation signals, translation initiation signals, starting codon, termination codon, transcription terminating signals, polyadenylation signals, and others. Suitable vectors are commercially available from a variety of companies. After the recombinant vectors containing BAL cDNA or gene is transfected into the host cells, they may remain as extrachromosomal DNA or they may be integrated into the host genome. In either case, they may direct the synthesis of recombinant BAL in the host cells. Some examples for the expression of heterogous genes are described in Methods in Enzymology, Vol. 153, Chapters 23 to 34 (Editors, R. Wu and L. Grossman, Academic Press, 1987). Large scale culture of the BAL synthesizing host cells and the purification of the enzyme may form a cost effective commercial means of production of BAL or the C-tail. Methods are well known to those skilled in the art for the large scale production of enzymes. Some examples of useful expression systems for the glycosylated C-tail of BAL are given below:

(1) Yeast and Fungi as host: The principles for the expression of recombinant BAL in the yeast are similar to that for E. coli expression. Examples are provided by Bitter, G. A. et al. in Methods in Enzymology (Wu and Grossman, eds.) 153:516–544 (1987)). Like E. coli, yeast host cells may express a foreign gene either in the cytosol or, preferably in this case, as secreted protein. Unlike E. coli expression, the secreted expression in yeast is capable of glycosylation. There are many vectors, promoters, and leaders available for yeast expression of secretion proteins. An excellent example is the system based on the control by alcohol oxidase promoter in methylotrophic yeast, Pichia pastoris. Vectors pHIL-S1 and pPIC9 are commercially available (Invitrogen) and can make large quantities of secretory eukaryotic recombinant proteins (1–4 mg per L of human serum albumin, Barr et al., Pharmaceutical Engineering 12:48–51, 1992; 12 mg per L of tetanus toxin fragment C, Clare, J. J. et al., Bio/Technology 9:455–460, 1991).

There are small numbers of fungal expression vectors which have been successfully used to express heterogous genes. The existing fungal expression vectors integrate themselves into the host genome after transfection (Cullen, D., Gray, G. L., and Berka, R. M., Molecular Cloning Vectors for Aspergillus and Neurospora, in A Survey of Molecular Cloning Vectors and their Uses, (Butterworth Publishers, Stoneham, Mass. 1986). When a leader is present in front of the expressed protein codons, the secreted recombinant proteins can be glycosylated. Some examples of successful expressions involve bovine chymosin (Cullen, D. et al. *Bio/Technology* 5:369–378 (1987)) and an acid protease from a different fungus (Gray, G. L., Hayenga, K., Cullen, D., Wilson, L. J., and Norton, S. *Gene* 48:41–53 (1987)).

(2) Insect cells as host: Baculovirus expression vectors for the synthesis of foreign genes in insect cells have been successfully used to express many mammalian and vital proteins as well as described for rat pancreatic BAL (DiPersio et al. *Protein Expr. Purif.* 3:114–120, 1992). This system is capable of glycosylation and can also express recombinant proteins at a high level. The use of this system has been reviewed in some detail (Luckow, V. A. and Summers, M. D., Trends in the Development of Baculovirus Expression Vectors, *Bio/Technology*, Sep. 11, 1987). Many of vectors derived from the baculovirus expression system are now commercially available, for example, vectors pBlueBacHis A, B, C and pEBVHis A, B, C as well as the insect host cells are available through Invitrogen.

(3) Mammalian cells as host: Many mammalian cell expression of heterogous genes have been successfully accomplished for commercial purposes. The commercial production of recombinant human tissue plasminogen activator is an example. Most of these expression vectors contains either mammalian promoter (such as metallocyanin or growth hormone) or vital promoters (such as SV40 early promoter or long terminal repeats of vital genes), polyadenylation signals, and appropriate regulatory elements for *E. coli*, cloning including antibiotic resistance genes. After the insertion of BAL downstream from the promoter, the vector can be first cloned in *E. coli*, isolated and transfected into mammalian cells. Neomycin or similar resistant selection markers can be either cotransfected into mammalian cells. Neomycin or similar resistant selection markers can be either cotransfected in another vector or in the same vector. For high level expression, a gene amplification system is advantageous. For example, the expression vector (or cotransfect) can contain the gene of dihydrofolate reductase (dhfr). When the dhfr− strain of Chinese hamster ovary (CHO) cells are used, the cloned gene can be coamplified with that of dhfr by adapting the transformed cells to increasing methotrexate concentration. The transformant clones secreting BAL can be identified by enzyme assays or by western blots. Successful examples of this approach include the synthesis of glycosylated recombinant prorenin (Poorman et al. *Proteins* 1:139–145 (1986)) and human immune interferon (Scahill, S. J. et al. *Proc. Natl. Acad. Sci., U.S.A* 80:4654–4658 (1983)).

(4) Expression of C-tail or BAL containing C-tail in transgenic animals: Technology already exists to transfer human BAL gene into the genomes of other animals for tissue specific expression (Jaenisch, R. *Science* 240:1468–1474 (1988); westphal, H. *FASEB J.* 3:117–120 (1989)). Some works are already in progress to alter the composition of milk by using transgenic technology (for review, see: Bremel, R. D., Yom, H. C. and Bleck, G. T. *J. Dairy Sci.* 72:2826–2833 (1989)). The general approaches, as summarized in the three reviews listed above, is to construct vectors containing promoters of secretory mammary gland (milk) proteins (such as casein or milk lysozyme), C-tail containing part of human BAL cDNA or gene, and appropriate complementing elements. The cloned vector is then microinjected into a newly fertilized egg of cow or sheep and the egg transferred to a 'foster mother' for the fetal development and birth. The transgenic offsprings are analyzed for gene transfer by Southern blots and for the production of human BAL in the milk. It is important to note that cows and sheep do not produce BAL in their milks. The transgenic animals can be interbred in order to produce a high yielding strain. The C-tail secreted in the milk would be fully glycosylated. Since cow and sheep do not make milk BAL, the recombinant product can be easily differentiated from the host milk proteins.

Sugar or sugar analogue containing compounds can also be synthesized by chemical reactions to mimic the C-tail structures. These can be used to bind the intestinal surface and compete with endogenous BAL in the same manner as the C-tail itself. The following examples demonstrate that galactose and fucose can elute endogenous bound BAL from rat intestinal surface, indicating that synthetic mimics of C-tail containing these sugars or their structural analogues can be used to affect the binding to intestinal surface. Since the C-tail contains repeating sequences and many glycosylation sites, the synthetic mimics can contain many sugar containing sites. The chemical linkages of sugars can be modeled based on the oligosaccharide structures of the C-tail, or the structural analogues of these oligosaccharide structures may contain essential features for effective binding to the intestinal BAL receptors. The sugars can be chemically attached to a polymer to create repeating units. Examples of suitable polymers include polypeptides, polyethylene glycol, dextran like sugar polymers and other synthetic polymers with appropriate functional groups for chemical linkage to sugars.

Pharmaceutical Applications and Compositions

As described in the examples below, it has been discovered that BAL binds through the oligosaccharides of its C-tail to lectin-like receptors on intestinal surface. This binding is an essential step in mediating cholesterol uptake by the intestine. Further, it has been discovered that the isolated C-tail of BAL can compete with BAL for binding to the receptors on the intestinal surface. It has further been shown that C-tail can competitively inhibit the intestinal uptake of cholesterol by reducing the intestinal bound BAL. The reduction of cholesterol uptake by C-tail is specific, since BAL is the only enzyme in the intestine that can mediate cholesterol uptake. BAL also hydrolyzes other fatty acid esters, and therefore can facilitate the uptake of other fats. The reduction of intestinal uptake of non-cholesterol fats by C-tail, however, is not specific since other lipases in the intestine can also digest non-cholesterol fats. Accordingly, BAL C-tail, as defined above, can be administered as a therapeutic agent to individuals in need of specific reduction of cholesterol uptake, and/or more general reduction in uptake of other fats, and thereby to treat hyperlipoproteinemia, hypercholesterolemia, and diseases associated with atherosclerosis.

In the preferred embodiment, the BAL C-tail is administered orally in an amount effective to reduce cholesterol intake from food as measured by a reduction in cholesterol levels in the blood. The dosage will vary depending on the formulation, the rate of excretion, individual variations such as the number of receptors on the intestinal surface, the cholesterol levels to be decreased, and the frequency of administration, as well as other factors routinely optimized by physicians.

The cholesterol uptake from diet by the intestine is about 200 mg/day/person. Cholesterol synthesized by the body is about 500 mg/day/person. The pancreas secrets cholesterol at about 500 mg/day/person, which is reabsorbed through the intestine. Thus, the C-tail competition at the intestinal surface must be effective to reduce the amount of cholesterol from an uptake of about 700 mg cholesterol/day/person. If the reduction is to a level less than 500 mg/day, the body reduce body cholesterol.

Pharmaceutical compositions containing BAL C-tail, designed to improve the pharmaceutical activity of C-tail when administered to a patient in an amount effective to reduce cholesterol uptake in the intestine and thereby decrease blood cholesterol levels, can be prepared in combination with appropriate pharmaceutical stabilization compounds, delivery vehicles, carriers, inert diluents, and/or other additives appropriate for enteral (oral) administration according to methods well known in the art. The formulation usually provides for release within the stomach or the intestine. The BAL C-tail can be formulated into a liquid, paste, suspension, gel, powders, tablets, capsules, food additives or other standard forms. Pharmaceutically compatible binding agents and/or adjuvant materials can be included as part of the composition. Examples include a binder such as microcrystalline cellulose, gum tragacanth, or gelatins an excipient such as starch or lactose; a disintegrating agent such as alginic acid, Primogen™, or corn starch; a lubricant such as magnesium stearate or sterotes; aglidant such as colloidal silicon dioxide; a sweetening agent such as sucrose or saccharin; and/or a flavoring agent such as peppermint, methyl salicylate, or orange flavoring. When the dosage unit form is a capsule, it can contain, in addition to material of the above type, a liquid carrier. Other dosage unit forms may further include coatings of sugar, shellac, or other enteric agents. The BAL C-tail can be administered as a component of a fluid such as an elixir, suspension, beverage, liquid dietary supplement or substitute, or syrup; or of a solid such as a wafer or candy. The BAL C-tail can also be mixed with other active materials that do not impair the desired action, or with materials that supplement the desired action, such as other blood lipid-lowering pharmaceutical compositions.

In one preferred embodiment, BAL C-tail is encapsulated within carriers that effect release in the small intestine, such as microparticles, microcapsules, or microspheres prepared from synthetic or natural polymers such as proteins, polyhydroxy acids, or polysaccharides. Appropriate systems are known to those skilled in the art. Several microsphere formulations have been proposed as a means for oral drug delivery. These formulations generally serve to protect the encapsulated compound and to deliver the compound into the blood stream. Enteric coated formulations have been widely used for many years to protect drugs administered orally, as well as to delay release. Other formulations designed to deliver compounds into the blood stream, as well as to protect the encapsulated drug, are formed of a hydrophobic protein, such as zein, as described in PCT/US90/06430 and PCT/US90/06433; "proteinoids", as described in U.S. Pat. No. 4,976,968 to Steiner; or synthetic polymers, as described in European Patent application 0 333 t23 by the UAB Research Foundation and Southern Research Institute. EPA 0 333 523 described microparticles of less than ten microns in diameter that contain antigens, for use in oral administration of vaccines. Larger sizes are preferred for the uses described herein to avoid uptake into the blood and lymph systems of the encapsulated BAL C-tail.

The microparticles can be formed of rapidly bioerodible polymers such as poly[lactide-co-glycolide], polyanhydrides, and polyorthoesters, whose carboxylic groups are exposed on the external surface as their smooth surface erodes; natural polymers such as proteins, like zein, modified zein, casein, gelatin, gluten, serum albumin, or collagen, and polysaccharides, like cellulose, dextrans, polyhyaluronic acid, polymers of acrylic and methacrylic esters and alginic acid; synthetic polymers such as polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes and copolymers thereof; and synthetically modified natural polymers such as alkyl celluloses, hydroxyalkyl celluloses, cellulose ethers, cellulose esters, and nitrocelluloses. Representative polymers include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl acetate), polyvinyl chloride, polystyrene, polyvinyl pyrrolidone, and polyvinylphenol. Specific representative bioerodible polymers include polylactides, polyglycolides and copolymers thereof, poly(ethylene terephthalate), poly(butyric acid), poly(valeric acid), poly(lactide-co-caprolactone), poly[lactide-co-glycolide], polyanhydrides, polyorthoesters, blends, and copolymers thereof.

These polymers can be obtained from sources such as Sigma Chemical Co., St. Louis, Mo., Polysciences, Warrenton, Pa., Aldrich, Milwaukee, Wis., Fluka, Ronkonkoma, N.Y., and BioRad, Richmond, Calif., or else synthesized from monomers obtained from these suppliers using standard techniques.

Pharmaceutical compositions containing BAL C-tail must be stable under the conditions of manufacture and storage and may be preserved against contamination by microorganisms, such as bacteria and fungi, through the use of antioxidants such as Vitamin E and ethoxyquin and bacteriostatic agents, which are on the list of compounds approved for use by the Food and Drug Administration.

As noted above, inactivation and excretion rates of the BAL C-tail, as well as other factors known to those of skill in the art, will affect the amount of drug which is administered to a patient. The determinative criteria is whether the amount is effective to reduce the blood choletetrol. Blood cholesterol levels are assayed by standard techniques used by clinical laboratories.

The BAL C-tail can be used to reduce the uptake of cholesterol by the intestine and thereby for the treatment of hyperlipidemias including hypercholesterolemia, hypertriglyseridemia and associated disease states such as atherosclerosis, cardiovascular disease, and pancreatitis. The BAL C-tail can also be used in normal subjects as a preventative measure to prevent the occurrence of these disorders. It is preferable that human serum cholesterol levels be maintained below 200 mg/dl, with values of 240 mg being considered clinically high and values of 160 mg being considered to be low.

The formulation is administered as a single daily dose or divided daily doses, most preferably three doses given before, during, or after meals. Patients can be maintained on BAL C-tail indefinitely to reduce the uptake of cholesterol by the intestine. Conditions to be considered in selecting dosage level, frequency, and duration primarily include the severity of the patient's disorder, the patient's serum cholesterol level, adverse side effects such as gastric distress, and the patient's need for preventive therapy, as well as the therapeutic efficacy. It is to be understood that for any particular subject, specific dosage regimens should be adjusted over time according to the individual patient need and the professional judgment of the person administering or supervising the administration of the compositions, and that the concentration ranges set forth herein are exemplary only and are not intended to limit the scope or practice of the claimed composition. Other concentration ranges and dosage durations can be determined by routine experimentation. An initial estimate of the dosage is based on the calculation that 20 µg is needed to block the receptor binding from I cm of the intestine and, therefore, 20 mg of C-tail should be enough to cover 10 meters in length of the intestine for blocking the BAL binding sites. A five-fold excess (100 mg) should be more than sufficient for preventing cholesterol absorption by the intestinal cells. Further adjustment of the dosage will be based on the monitoring of the dosage response of patients to C-tail in lowering blood cholesterol.

The present invention will be further understood with reference to the following non-limiting examples. All literature citations are expressly incorporated herein by reference.

EXAMPLE 1

Proline-rich Domain and Glycosylation are not Essential for the Enzymatic Activity of Bile Salt-activated Lipase.

To test the functional requirements of the structural regions in the BAL molecule, the truncated human milk bile salt-activated lipase (T-BAL) cDNA (without the mucin-like caroxy terminal region, residues 539–722) was expressed from the T7 system in *Escherichia coli* and purified, and the properties of the truncated recombinant enzyme were studied. The methods were as follows.

Abbreviations

The following abbreviations are used in this example: PANA, p-nitrophenyl acetate; PANB, p-nitrophenyl butyrate; SDS, sodium dodecyl sulfate; T-BAL, truncated form of bile salt-activated lipase; PCR, polymerase chain reaction; TN (50 mM Tris-HCl, pH 8.0, and 100 mM NaCl); EGTA, ethylene glycol-bis(β-aminoethyl ether)N,N,N',N'-tetraacetic acid; FPLC, fast protein liquid chromatography; and BSA, bovine serum albumin.

Materials

The purification of BAL from human milk was performed as described in Baba, T., et al., Biochemistry 30:500–510 (1991), incorporated herein by reference. The λgt10 cNDA library from human lactating breast tissue was purchased from Clontech (Palo Alto, Calif.). Glycerol tri[9,10-$^3$H] oleate was obtained from Amersham (Arlington Heights, Ill.). The oligonucleotides Primer I and Primer II, were prepared by Dr. K. Jackson in the Molecular Biology Resource Facility, Oklahoma University Health Science Center. All other chemicals were purchased from Sigma Chemical Co. (St. Louis, Mo.).

Molecular Biology Methods

Standard methods for sequencing analyses, restriction enzyme treatments, ligation, and subcloning, as described in commonly known and used reference technique publications, Sambrook J., E. F. Fritsch, and T. Maniatis, *Molecular Cloning, A Laboratory Manual*, Cold Spring Harbor Laboratory Press, Cold Spring Harbor, N.Y. (1989); and Ausuble, F. M., et al. (Eds.), *Current Protocols in Molecular Biology*, Green Publishing Associates and Wiley-Interscience, New York, N.Y. (1989). The cDNA clones G10-2 and G10-5 were isolated from human mammary gland cDNA as described in U.S. Pat. No. 5,200,183 to Tang and Wang. DNA sequencing analyses were performed using a DNA sequencing kit from United States Biochemical Corp. (Cleveland, Ohio) as described below. Double stranded DNA templates were first denatured as described by Kraft et al., *BioTechniques* 6:544–547 (1988). Then 2.5 µg of DNA, 15 ng of primer and 2 µl of reaction buffer were combined in a total volume of 10 µl and heated to 65° C. for 2 min, then cooled to 25° C. over a period 30 min to anneal the template. Labeling mixture was diluted 5-fold with water and Sequenase version 2.0 was diluted 8-fold with water. 1 µl of DTT (0.1M), 2 µl of diluted labeling mix, 5 µCi of [α$^{32}$P]dATP and 2 µl of diluted Sequenase were added to the annealed template-primer. After mixing the tubes were incubated at room temperature for 3 minutes. 2.5 µl of the termination mixture were placed in tubes. The tubes were pre-warmed at 37° C. for 1 minutes. 3.5 µl of labeling reaction mixture was transferred to each termination tube, mixed and then incubated at 37° C. for 3 minutes. The reactions were stopped by adding 4 µl of stop solution. Samples were then run on a 6% acrylamide gel. Prior to the application of samples, the gel was pre-run at a constant voltage of 2000 volts for 30 minutes. Samples were heated at 75° C. for 2 minutes immediately before loading 2 µl onto the sequencing gel. The gels was run at a constant voltage of 2000 for 3 to 4 hours. After the run, the gel was transferred 3 MM paper then dried at 80° C. under vacuum for 2 hours. Kodak X-Omat™ PR film was exposed at room temperature overnight for the subsequent reading of the DNA sequence. PCR was performed as described by Innis, M. A., and D. H. Gelfand, in PCR Protocols. A Guide to Methods and Application 3–12, Innis, M. A., et al. (Eds.), Academic Press, New York, N.Y. (1990), incorporated herein by reference. The PCR generated DNA was subcloned into PCRII using the TA cloning kit from Invitrogen (San Diego, Calif.) as described below. Ligation with the PCRII vector were set up as 1:1 and 1:3 molar ratio of vector:PCR product. 1 µl of 10× ligation buffer, 50 ng of vector, PCR product and 4 units of T$_4$ DNA ligase were combined in a total volume of 10 µl. The ligation reaction were incubated at 12° C. overnight. 1 µl of each ligation reaction was then added to 50 µl of INVαF' competent cells containing 2 µl of 0.5M β-mercarptoethanol. The tubes were incubated on ice for 30 minutes. The tubes were then placed in a 42° C. water bath for 30 seconds then returned to ice for 2 minutes. 450 µl of room temperature SOC was added to each tube. The tubes were then incubated at 37° C., and shaken at 225 rpm for 1 hour. The transformed cells were spread onto LB plates containing 50 µg/ml kanamycin and i mg of X-Gal. The plates were then inverted and incubated at 37° C. overnight for the selection of the transformed clones. Plasmid isolation was performed using the Magic Miniprep™ system supplied by Promega (Madison, Wis.). Three ml of overnight culture was centrifuged at 4000 rpm for 5 minutes to pellet the cells. The pellet was suspended in 200 µl of Cell Resuspension Solution. 200 µl of cell lysis solution was added and mixed by inverting the tubes until the suspension cleared. 200 µl of Neutralization Solution was added and mixed by inverting the tubes several times. A Minicolumn was attached to a syringe barrel and the assembly was inserted into a vacuum manifold. The resin/DNA mixture was transferred to the syringe barrel and poured into the column by applying vacuum. The column was washed with 2 ml of Column Wash Solution and the resin was dried. The minicolumn was centrifuged at 14000 rpm for 20 sec. to remove the remaining wash solution. The DNA was eluted from the column by applying 50 µl of 70° C. water to the column then centrifuge the column after 1 minute for 20 seconds.

Construction of Vector

The unique SmaI restriction site of the overlapping clones G10-2 and G10-5 was utilized for construction of the cDNA G10-6 to encompass the entire coding sequence region of BAL. PCR was used for preparing T-BAL cDNA with the use of Primers I and II for expression of the truncated form of BAL. The T-BAL cDNA was ligated to the pET11a cloning vector (Invitrogen, San Diego, Calif.) at the NdeI/BamHI cloning site for the subsequent expression of T-BAL using the T7-expression system in E. coli.

Expression of T-BAL Using pET11a Vector.

The general approach and methodology for using T7 polymerase to direct the expression of the cloned genes are described by Studier, F. W., et al., Methods Enzymol. 185:60–89 (1990), incorporated herein by reference. The cDNA of T-BAL was ligated to the NdeI/BamHI cloning sites of pET11a (Novagen, Madison, Wis.). The vector was used to transform the E. coli BL21 (DE3) for the expression of T-BAL. The cells harboring the vector were cultured overnight in ZB medium (Studier et al. (1990)) with ampicillin. The next morning 4 liters of LB-ampicillin were incubated with 80 ml of the overnight culture, which was shaken at 37° C. until absorbance at 600 nm reached 0.6. Isopropyl-β-D-thiogalactopyranoside was then added to a concentration of 0.4 mM with shaking for 3 hours. The cells were collected by centrifugation and resuspended in 800 ml TN buffer (50 mM Tris-HCl, pH 8.0, and 100 mM NaCl) with 80 mg lysozyme. The mixture was frozen at −70° C. and then thawed in a 37° C. water bath, for three cycles. The solution was diluted to 2,400 ml with TN and centrifuged at 16.000×g for 15 minutes. The pellet (inclusion bodies) was then washed twice with Triton™ X-100 (0.1%) in TN, and the pellets recovered by centrifugation and kept frozen at −20° C. for further processing.

Refolding and Purification of T-BAL

The frozen inclusion bodies were further solubilized by stirring with 60 ml of 8M urea in 100 mM Tris-HCl, pH 12.5, containing 1 mM EGTA (ethylene glycol-b(β-aminoethyl ether)N,N,N',N'-tetraacetic acid), 10 mM β-mercaptoethanol and 5% glycerol (v/v). This mixture was centrifuged at 105,000×g for 30 minutes, and the supernatant was then placed in a dialysis tubing (exclusion MW=10,000) and dialyzed against 1 liter of a refolding buffer containing 1M urea, 0.1 mM β-mercaptoethanol, and 5% glycerol in 10 mM Tris-HCl, pH 8.0. After dialysis for 20 hours, the refolded T-BAL was assayed for esterase activity, as described under "Esterase Assay" below, using 1 mM PANA as substrate and 2 mM taurocholate as activator to determine the amount of active enzyme in the dialyzed solution. The refolded T-BAL was then mixed with 60 ml of saturated ammonium sulfate (adjusted to pH 8.0 with NH$_4$OH), which caused the precipitation of T-BAL. The T-BAL was collected from the precipitate after centrifugation at 18,000 rpm for 1 hour. The collected precipitate was solubilized with 40 ml of the refolding buffer and stirred at 4° C. for 30 minutes. The supernatant fraction was then concentrated to 3 to 5 ml in an Amicon Centriprep™-10 concentrator (Beverly, Mass.). After further ultracentrifugation at 105,000×g for 30 minutes, the supernatant fraction (1 ml) was subjected to molecular sieving fractionation by fast protein liquid chromatography (FPLC). Two Superose™ 12 columns (Pharmacia, Piscataway, N.J.) were linked in tandem for the FPLC fractionation. The columns were equilibrated and eluted with a buffer solution containing 1M urea, 0.15M NaCl, 0.1 mM β-mercaptoethanol, and 50 mM Tris-HCl, pH 8.0. The column was eluted with a flow rate of 0.5 ml/minutes. The eluate was collected in 1 ml fractions and monitored by measuring absorbance at 280 nm and by assaying esterase activity with PANA as substrate.

N-terminal Amino Acid Sequence Analysis

Automated Edman degradations were performed according to Hewick, R. M. et al., J. Biol. Chem. 256:7990–7997 (1981), incorporated herein by reference, in a Model 470A gas-phase protein sequencer equipped with a Model 120A on-line phenylthiohydantoin amino acid analyzer (Applied Biosystems, Inc., Foster City, Calif).

Esterase Assay

The kinetic studies of BAL esterase activity with short chain esters were performed using p-nitrophenyl acetate (PANA) and p-nitrophenyl butyrate (PANB) as substrates, as described in Wang, Biochem. J. 279:297–302, (1991), incorporated herein by reference. For deducing the Michaelis-Menten kinetic parameters, the experiments were performed at 25° C., and the range of the substrate concentration in the final assay mixtures was 0.4 to 2 mM for PANA and 0.1 to 0.5 mM for PANB, with 2 mM taurocholate as activator. The rate of p-nitrophenol production was determined from the initial portion of the absorbance change (20 seconds) at 418 nm using a Hewlett-Packard Diode Array Spectrophotometer (Hewlett Packard, Palo Alto, Calif.) equipped with a peltier temperature control. For monitoring the refolding efficiency, as well as the esterase activity in column chromatography eluants and the specific activity of the purified enzyme, the enzyme assays were performed with 1 mM PANA as substrate and 2 mM taurocholate as activator. One unit of enzyme activity was defined as one μmole of the product released per minute.

Thermostability of T-BAL

For determining the thermostability, 0.1 mg/ml each of T-BAL and native BAL in sodium phosphate (0.15M, pH 7.4) were incubated for 10 minutes An a water bath at 30° C., 40° C., 45° C. and 50° C. for 10 minutes. After incubation, the solutions were cooled in ice-water. These treated samples were then assayed for remaining activity with PANA as substrate.

Lipase Assay

The lipase assay of BAL was performed according to a modification of the method of Nilsson-Ehle, P., and M. C. Schotz, J. Lipid Res. 17:536–541 (1976), incorporated herein by reference, using glycerol tri[9,10-$^3$H]oleate as substrate. The two-fold concentrated stock substrate solution was prepared by emulsifying 28 μmol of trioleoylglycerol (specific activity 1.4 μCi/μmol) and 2.8 μmol of dioleoylphosphatidylcholine in 10 ml of 50 mM NH$_4$OH—HCl buffer, pH 8.5. The mixture was emulsified using a W-380 sonicator (Heat Systems-Ultrasonics, Inc., Farmingdale, N.Y.) at a setting of 5 (50% maximum output) for 30 seconds in an ice bath. After cooling, the mixture was further sonicated for an additional 30 seconds. The assay mixture with final volume of 100 μl contained 50 mM NH$_4$OH-HCl buffer, pH 8.5, 1.4 mM trioleoylglycerol, 0.14 mM dioleoylphosphatidylglycerol, taurocholate, and 10 μl of the enzyme solution. Following a one-hour incubation at 37° C. with agitation, the reaction was terminated by the addition of 3.2 ml of chloroform-heptane-methanol (5:4:5.6, vol/vol/vol) and 1 ml of 0.2M NaOH. Samples were centrifuged and mixed with 10 ml of Hydrocount™ (J. T. Baker, Inc., Phillipsburg, N.J.), and the radioactivity was determined in a Beckman scintillation counter (Fullerton, Calif.).

Sodium Dodecyl Sulfate (SDS)-Polyacrylamide Gel Electrophoresis

The SDS-polyacrylamide gel electrophoresis was performed using the LKB-Pharmacia Phast system (Piscataway, N.J.) and with a 8–25% polyacrylamide gel slab manufactured by Pharmacia (Piscataway, N.J.). The samples were treated with 10 mM β-mercaptoethanol and 2% SDS at 100° C. for 6 minutes prior to electrophoresis.

Protein Assay

The protein content of the enzyme preparation was determined by a modification (Wang, C.-S., and R. L. Smith, *Anal. Biochem.* 63:414–417 (1975), incorporated herein by reference, of Lowry's procedure using serum albumin as standard (Lowry O. H. et.al. *J. Biol. chem.* 193:265 (1951).

Fluorescence Measurement of the Interaction of T-BAL with Taurocholate

Fluorescence measurements of the interaction of T-BAL with taurocholate were made at 25° C. with the aminco-Bowman Series 2 Fluorescence Spectrometer (Urbana, Ill.). The T-BAL tryptophanyl fluorescence was used for studying the interaction of T-BAL with taurocholate. Fluorescence was recorded at 340 nm with excitation wave length at 280 nm. The band-width of excitation and emission were both set a 2 nm. The sensitivity of the instrument was set at 1,000 volts of the detector high voltage.

When taurocholate (the activator) was not present, the fluorescence intensity of T-BAL was $F^o$. At the saturating concentration of taurocholate, the fluorescence intensity was $F_\infty$. Based on the fluorescence (F) at a specified taurocholate concentration, the molar fraction (x) of T-BAL that is associated with taurocholate was determined by relating the F, as shown in the following equation:

$$F = (1-x)F_o + xF_\infty$$

The deduced molar fraction (x) is then used for calculation of the taurocholate and T-BAL binary complex dissociation constant $K_A$. Conversely, the computer least-square curve-fitting procedure to treat $K_A$ and $F_\infty$ as the variable parameters can be used for achieving the best agreement with the calculated and the experimentally determined values of F.

Data Analysis

Kinetic analysis of data generated in these experiments was performed using a LOTUS 1-2-3 SPREAD SHEET program (Worcester, Mass.) and an IBM-AT computer. The performance of least-square non-linear curve fitting was done according to the approach described by Bevington, P. R., in *Data Reduction and Error Analysis for the Physical Sciences* 56–65 and 204–246, McGraw-Hill, New York (1969), incorporated herein by reference.

(a) The carboxyl-terminal domain, O-glycosylation, and N-glycosylation are not essential for the enzymatic function of BAL The amino acid sequence of native human milk BAL cDNA (Baba, T., et al., *Biochemistry* 30:500–510 (1991); Hui, D. Y., and J. A. Kissel, *FEBS Lett.* 276:131–134 (1990); Nilsson, J., et al., *Eur. J. Biochem.* 192:543–550 (1990)) encodes for a 722-residue mature enzyme and is shown in Sequence ID No. 3. The cDNA structure is identical to that of the pancreatic BAL (Reue, K., et al., *J. Lipid Res.* 32:267–276 (1991)), supporting the concept that the enzyme from mammary gland and from pancreas are expressed from the same gene.

As expected, the T-BAL synthesized in *E. coli* is inactive and is insoluble in aqueous buffer. Active T-BAL was obtained by refolding. This procedure included the solubilization of the inclusion bodies with urea and β-mercaptoethanol at a high pH (12.5), followed by dialysis against a low concentration of urea at lower pH (8.0). Based on the enzyme activity measurement, the yield of the active enzyme was about 10 mg per 4 liters of the cultured LB-medium. SDS-polyacrylamide gel electrophoresis gave rise to a major protein (greater than 90%) in the urea-soluble fraction corresponding to a molecular weight of 60,000, which approximated closely the expected molecular weight of T-BAL (59,270). N-terminal sequence analysis of this protein fraction gave the expected BAL N-terminal sequence of Ala-Lys-Leu-Gly-Ala-Val-Tyr-Thr-, indicating the successful synthesis of T-BAL and the removal of initiation methionine. The specific activity of T-BAL after the initial step of the refolding was about 5 to 10 units/mg, which is only 10 to 20% of that of the native BAL.

The recombinant T-BAL expressed in *E. coli* is not glycosylated, indicating further that the highly glycosylated C-terminal region of BAL is not essential for catalytic function.

Purification of T-BAL was achieved by molecular sieving with FPLC after prior partial purification of the refolded T-BAL with ammonium sulfate precipitation. Two major peaks were found in the column fractions. The first peak, eluted at the void volume (17 ml), represents the major protein peak and contains mainly the aggregate form of the inactive T-BAL. The second peak (eluted at 28 ml) contains BAL activity. SDS-polyacrylamide gel patterns of fractions 27–29 indicate that T-BAL eluted in this peak was homogeneous. From four individual batches, an average specific activity of 64±2 units/mg for the purified enzyme (fraction 28) was obtained. The FPLC column chromatography effectively separated the active from the inactive forms of the enzyme, since this specific activity of T-BAL is higher than that reported for the native BAL (52 units/mg) reported previously (Wang & Johnson (1983)).

(b) Kinetic and specificity

With the availability of a sufficient amount of purified recombinant T-BAL, the specificity and kinetics of T-BAL and the native BAL were compared and other characteristics were noted.

Thermostability of T-BAL

To compare the stability of T-BAL with the native enzyme, these two enzyme forms were treated at temperatures ranging for 30° C. to 50° C. The heat inactivation patterns for T-BAL and native BAL were similar, with both showing a loss of about 90% of activity with treatment at 50° C. for 10 minutes. This further suggests that the folding of T-BAL is similar to that of the catalytic domain of the native enzyme.

Taurocholate Binding Kinetics of T-BAL

The dissociation constants $K_A$ of T-BAL and native BAL are similar. In a direct binding study of the tryptophanyl fluorescence upon interaction with taurocholate, native BAL upon binding with the bile salt showed about 20% decrease of the protein tryptophanyl fluorescence at a saturating concentration of taurocholate (Wang & Kloer (1983)), which probably resulted from a conformational change of BAL upon ligand binding. The dissociation constant of native BAL is 0.37 mM. (Wang, C.-S., *J. Biol. Chem.* 256:10198–10202 (1981)). A similar decrease of tryptophanyl fluorescence was observed with T-BAL, in which α and β are the two parameters utilized for expressing the activation effect of taurocholate by modifying the kinetic parameters $K_S$ and $k_{cat}$, respectively (Segel, I. H., in *Enzyme Kinetics* 227–231, John Wiley & Sons, New York (1975)). Based on a 1:1 stoichiometry, the dissociation constant $K_A$ of 0.32±0.03 mM (n=4) was determined for the T-BAL and taurocholate interaction. There was an 18% decrease of fluorescence intensity at a saturating concentration of taurocholate. Thus, T-BAL has a slightly higher affinity to the monomeric form of taurocholate compared with the native enzyme. These results indicate that the microenvironment of taurocholate binding sites of T-BAL and native BAL are very similar despite the deletion of the proline-rich sequence domain of T-BAL.

Kinetic Properties of T-BAL with PANA and PANB

Further kinetic analysis indicated that there are enzyme specificity changes revealed with the use of PANA and PANB (p-ntirophenyl butyrate) as substrates.

Similar to the native BAL, T-BAL was found to contain basal activity when assayed in the absence of bile salts with the esterase substrates. Therefore, taurocholate can also be considered as a non-essential activator of T-BAL. From the Lineweaver-Burke plots, the kinetic parameters $K_S$, $k_{cat}$ (for basal enzyme) and $\alpha K_S$, and $\beta k_{cat}$ (taurocholate-activated enzyme) for T-BAL and PANA and PANB as substrates were obtained. Despite the fact that a slightly higher specific activity of T-BAL (64 units/mg) than that of native enzyme (52 units/mg) (Wang & Johnson (1983)) was obtained, the derived $k_{cat}$ and $\beta k_{cat}$ of T-BAL was about 2 to 8 fold lower than that of the native enzyme. However, the deduced $K_S$ and $\alpha K_S$ of T-BAL were only slightly higher than that of the native enzyme. Thus, the presence of the proline-rich sequence plays a role mainly in enhancing the turnover rate of the enzyme, but has only a minor effect on the substrate binding affinity. In addition, there is a change of the preferential reactivity of the enzyme. Previously it was reported that among the short chain acyl-esters of p-nitrophenol, native BAL has the highest $k_{cat}$ and $\beta k_{cat}$ with PANB. In contrast, T-BAL has a higher $k_{cat}$ and $\beta k_{cat}$ with PANA than with PANB, when assayed in the presence of taurocholate. Despite this, T-BAL also has higher substrate specificity constants ($k_{cat}/K_S$ and $\beta k_{cat}/\alpha K_S$ of T-BAL with PANB. This is similar to what is found for the native enzyme. The activation effect of taurocholate on BAL-catalyzed hydrolytic reaction with PANA as substrate demonstrates that the proline-rich domain of BAL does not represent the bile salt-binding site of the enzyme.

Lipase Activity of T-BAL

There is an essential requirement of bile salt micelles acting as fatty acid acceptors in the native BAL-catalyzed hydrolysis of long chain triacylglycerol (Wang et al. (1988)). The hydrolysis of glycerol was compared in native BAL and T-BAL. In this respect, T-BAL was found to have a requirement similar to that of native BAL for a bile salt in the hydrolysis of long-chain trioleoylglycerol. Since serum albumin is not a fatty acid acceptor for BAL catalysis, it is also a poor fatty acid acceptor in the BAL-catalyzed reaction; thus only taurocholate, and not BSA, was included in the lipase mixture as the fatty acid acceptor.

There is an apparent saturation of activation of the native BAL catalysis when taurocholate concentration is above 60 mM, attributable to the partial inactivation of the native BAL when taurocholate concentration is high. In contrast, there was apparent non-saturable activation of T-BAL by micellar taurocholate (up to 120 mM taurocholate tested). The apparent saturation of the activation by taurocholate above 60 mM, on the other hand, is likely due to the partial inactivation of the enzyme when the taurocholate concentration is high. These results indicate that the transfer of fatty acid product from the enzyme active site is probably not through a receptor mediated process but through second order reaction kinetics involving the enzyme-fatty acid complex and the taurocholate micelles.

EXAMPLE 2

The Function of the C-Tail of BAL is to Bind BAL to the Intestinal Epithelial Lining Cells.

(a) Binding of human milk BAL to intestinal mucosa.

Experiments were conducted to determine that human milk BAL binds to the intestinal mucosa by (i) radiolabeling ($I^{125}$) purified native human milk BAL, (ii) incubating radio-labeled BAL inside isolated mouse intestine, (iii) determining the extent of intestinal retention of labeled BAL, and (iv) examining the mechanism of binding the BAL to intestine by examining the elution of the mouse endogeneous BAL with galactose, fucose, heparin, 0.3M NaCl and with using isotonic phosphate buffer as control.

Methods

Purification of human milk BAL was performed as described by Wang, C-S., and K. Johnson, "Purification of human milk bile salt-activated lipase," Anal. Biochem. 133:457–461 (1983), incorporated herein by reference. Preparation of a truncated form of recombinant BAL (T-BAL) was performed as described in Example 1.

The iodination of human milk BAL and recombinant T-BAL was performed using iodo beads (Pierce, Rockfold, Ill). Iodine$^{125}$ was obtained from Amersham (Arlington Heights, Ill). The iodination was performed by adding 6 µl of $^{125}$I to 94 µl of the enzyme solution (2 mg/ml in sodium phosphate buffer, pH 6.5). One washed bead was placed in the solution and let stand at room temperature for 15 minutes. The mixture was then passed through a Bio-spin™ 6 column (Bio Rad, (Hercules, Calif.) and centrifuged at 2275 rpm for 4 minutes at 4° C. and the eluate collected. The eluate was diluted with 400 µl of 0.1M sodium phosphate buffer, pH 6.5. The eluted fractions were combined and 1 µl of the eluate was examined for radioactivity. The lipase assay of BAL was performed a described in Example 1 using glycerol tri[9,10-$^3$H]oleate as substrate. The two-fold concentrated stock substrate solution was prepared by emulsifying 28 µmol of trioleoylglycerol (specific activity 1.4 µCi/µmol) and 2.8 µmol of dioleoylphosphatidylcholine in 10 ml of 50 mM NH$_4$OH—HCl buffer, pH 8.5. The mixture was emulsified using a W-380 sonicator (Heat Systems-Ultrasonics, Inc., Farmingdale, N.Y.) at a setting of 5 (50% maximum output) for 30 seconds in an ice bath. After cooling, the mixture was further sonicated for an additional 30 seconds. The assay mixture with final volume of 100 µl contained 50 mM NH$_4$OH—HCl buffer, pH 8.5, 1.4 mM trioleoylglycerol, 0.14 mM dioleoylphosphatidylglycerol, 30 mM taurocholate, and 10 µl of the enzyme solution. Following a one hour incubation at 37° C. with agitation, the reaction was terminated by the addition of 3.2 ml of chloroform-heptane-methanol (5:4:5.6, vol/vol/vol) and 1 ml of 0.2M NaOH. Samples were centrifuged and mixed with 10 ml of Hydrocount™ (J. T. Baker, Inc., Phillipsburg, N.J.), and the radioactivity was determined in a Beckman scintillation counter (Fullerton, Calif.).

Protocol for binding of $^{125}$I-labeled BAL and T-BAL to mouse small intestine The duodenum and jejunum were removed from mouse (about 20 grams each) small intestine and cut into 12-cm segments. Three experiments were performed in which T-BAL, without the C-tail, was used in parallel experiments as a control. The segments were washed once with 0.15M NaCl and twice with 0.1M sodium phosphate buffer, pH 6.5. Twenty µl of the labeled samples were first mixed with 20 µl of 8M urea and then diluted with 720 µl distilled water and 240 µl 20% albumin with a final volume of 1 ml. Five hundred µl of the solution were then injected into each intestinal segment with both ends ligated. The segments were incubated at room temperature for two hours. After incubation, the intestine was washed three times with 0.1M sodium phosphate buffer, pH 6.5, and 2 cm of the intestinal pieces were cut for counting the radioactivity.

Figure 2:
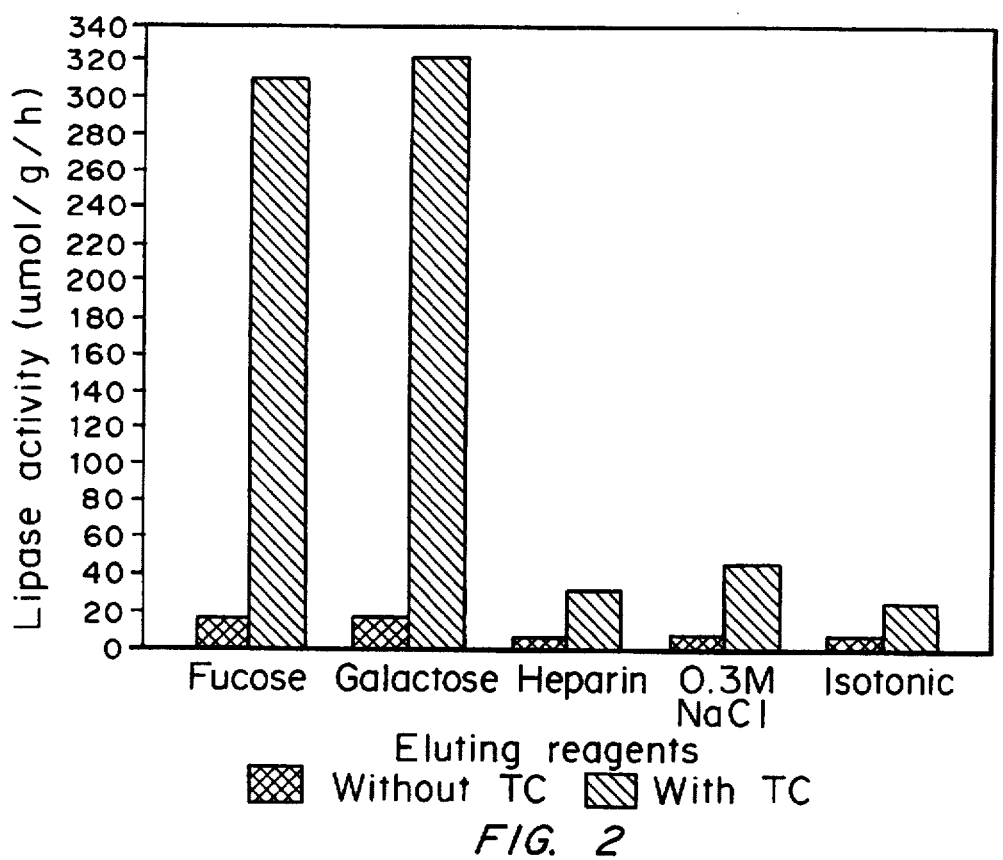
FIG. 2 shows the solution of endogenous BAL lipolytic activity, measured in μmol/g/h from mouse intestinal mucosa using either isotonic phosphate buffer, fucose (0.1M), galactose (0.1M), heparin (10 mg/ml), or NaCl (0.3M).

The results of these experiments are shown in Table I, Table II, and Table III, and in FIG. 2.

TABLE I

Binding of $I^{125}$-labeled BAL and T-BAL to mouse small intestine.

| | BAL | T-BAL |
|---|---|---|
| | Bound ng/cm | |
| Exp. 1 | 272 | 42 |
| Exp. 2 | 353 | 31 |
| Exp. 3 | 527 | 25 |
| Mean | 384 | 33 |
| ±SD | 130 | 9 |

Average from 3 experiments.

TABLE II

Individual experiments examining binding of $I^{125}$-labeled BAL and T-BAL to mouse small intestine.

| Experiment 1 | | Experiment 2 | | Experiment 3 | |
|---|---|---|---|---|---|
| BAL (ng/cm) | T-BAL (ng/cm) | BAL (ng/cm) | T-BAL (ng/cm) | BAL (ng/cm) | T-BAL (ng/cm) |
| 286 | 57 | 424 | 47 | 568 | 0.41 |
| 346 | 41 | 488 | 32 | 494 | 13.62 |
| 284 | 32 | 275 | 32 | 312 | 44.73 |
| 172 | 39 | 224 | 12 | 734 | 41.27 |
| Mean | | | | | |
| 272 ± 73 | 42 ± 11 | 353 ± 124 | 31 ± 14 | 527 175 | 25 22 |

In these experiments, native BAL was retained by the intestinal mucosa in amounts nearly twelve times greater than T-BAL, as shown in Table I and Table II. Since the native BAL and T-BAL differ only in C-tail, these results indicate that the attachment to intestinal surface is mediated by the glycosylated C-tail, possible to a receptor on the intestinal surface.

To determine whether pancreatic BAL attaches to the surface of the intestine in an adult animal, BAL enzymatic activity was measured in mouse intestine after the segments were thoroughly washed with physiological saline. The results demonstrated that the intestine possessed high BAL activity.

To examine the nature of interaction between BAL and the mouse small intestine receptor, experiments were conducted to elute the endogenously bound BAL enzymatic activity from the intestinal mucosa by incubating a 1 cm segment of the washed intestine with fucose, galactose, heparin, NaCl and isotonic phosphate buffer. The results are shown in Table III.

TABLE III

Elution of mouse endogenous pancreatic BAL from mouse small intestine.

Elution Buffer:

| Fucose (0.2M) | Galactose (0.2M) | Heparin (10 mg/ml) | 0.3M NaCl | Isotonic phosphate buffer |
|---|---|---|---|---|
| | | Lipase activity (μmol/g/hr) | | |
| Trial 1: | | | | |
| 20[a] | 393[b] | 20[a] 411[b] | 7.7[a] 32.2[b] | 8.8[a] 46.7[b] |
| Trial 2: | | | | |
| 13[a] | 357[b] | 20[a] 300[b] | | 7.9[a] 25.8[b] |
| Trial 3: | | | | |

TABLE III-continued

Elution of mouse endogenous pancreatic BAL from mouse small intestine.

Elution Buffer:

| Fucose (0.2M) | Galactose (0.2M) | Heparin (10 mg/ml) | 0.3M NaCl | Isotonic phosphate buffer |
|---|---|---|---|---|
| | | Lipase activity (μmol/g/hr) | | |
| 16[a] | 276[b] | 16[a] 154[b] | | |
| Average: | | | | |
| 16 | 309 | 19 322 | 7.7 | 8.8 7.9 |
| Standard | | | 32.2 | 46.7 25.8 |
| deviation: | | | | |
| 4 | 74 | 2 81 | | |

[a]without taurocholate (a bile salt); assay for non-specific lipase activity.
[b]with taurocholate; assay for specific BAL activity.

Only low activity of BAL was eluted with isotonic phosphate buffer and with 0.3M NaCl, indicating that BAL is not bound to intestine through ionic interactions. Further, heparin did not elute more BAL activity than those eluted by the isotonic phosphate buffer and by NaCl, indicating that the intestinal binding activity of BAL, which is known to bind heparin, mediated by heparin is not significant. When elution was carried out with either galactose or fucose, however, a large amount of BAL activity was eluted. These results indicate that the binding of BAL to the intestinal lumenal surface is through the oligosaccharide groups in the C-tail. Further, since the elution is very specific, the results suggest the presence of a receptor (CT receptor) that specifically binds the oligosaccharides in the C-tail of BAL.

Mouse pancreatic BAL has a C-terminal region containing four repeating motifs similar to that of the human enzyme. The results above confirm a similarity in the structure of the oligosaccharides, since human BAL binds to mouse intestine.

EXAMPLE 3

(a) The elution of rat endogeneous intestinal BAL with galactose, fucose,methyl-α-mannoside, EGTA, heparin and with isotonic phosphate buffer as control Because the intestine from mouse is too small in size, rat intestine was used to demonstrate the elution of BAL by various compounds. The initial experiment was to demonstrate that, like the observation done with mouse intestine, the rat endogeneous BAL can also be similarly eluted with galactose and fucose. Since calcium ion is required for the ligand binding of C-type lectin, EGTA elution was included for a test of calcium requirement for the BAL binding to intestinal surface.

Table IV shows the results of three experiments which indicate that bound rat intestinal BAL was eluted by galactose (0.1M), fucose (0.1M) and EGTA (1 mM). The elution by heparin (10 mg/ml) was ineffective as the activity in the eluent was low, similar to the level of elution by isotonic phosphate buffer (pH 7.4). In these experiments, 1 cm-segments of the washed rat intestine were incubated for 30 min at room temperature with the eluting compounds dissolved in isotonic phosphate buffer, pH 7.4. The BAL activity in the eluent was assayed as indicated in Example 1.

TABLE IV

Elution of rat intestinal BAL with various reagents.

| | galactose (0.1M) | fucose (0.1M) | EGTA (1 mM) | heparin (10 mg/ml) | isotonic buffer |
|---|---|---|---|---|---|
| | BAL activity (μmol/g intestine/h) | | | | |
| EXP1 | 13.01 | 24.25 | 14.54 | 2.09 | 0.99 |
| EXP2 | 16.44 | 26.92 | 21.67 | 1.82 | 0.52 |
| EXP3 | 22.91 | 13.61 | 19.59 | 1.98 | 1.82 |
| AVERAGE = | 17.45 | 21.59 | 18.60 | 1.96 | 1.11 |
| SD = | 3.02 | 7.04 | 3.66 | 0.14 | 0.66 |

The failure of heparin to elute the intestinal bound BAL indicated that BAL is not bound to rat intestine through heparin. These results are in total agreement with the results obtained on the elution of BAL from mouse intestine (Table III). The successful solution of bound BAL by either galactose or fucose indicates that the binding of BAL to the intestinal lumenal surface is through the oligosaccharide groups in the C-tail. The finding of EGTA eluted BAL indicated the binding of BAL-tail to intestine has a calcium cofactor requirement.

(b) The release of BAL from intestinal epithelial cells was associated with a diminished cholesterol uptake from cholesterol oleate Experimental Experiments were conducted to demonstrate that the attachment of BAL to the intestinal lining cells is required for the uptake of cholesterol as follows.

A cholesterol (oleate)ester emulsion solution was prepared as follows. A two-fold concentrated cholesterol oleate stock solution was prepared by emulsifying 6 μmol of [$^3$H] cholesterol oleate (1.6 μCi/μmol) (Amersham, Arlington Heights, Ill.) with 0.6 μmol of dioleoylphosphatidylcholine in 15 ml of isotonic phosphate buffer, pH 7.4. The mixture was emulsified using a W380 sonicator (Heat System-Ultrasonics, Inc. (Farmingdale, N.Y.) at a setting of 5 (50% maximum output) for 30 seconds in an ice bath. After cooling, the mixture was further sonicated for an additional 30 seconds.

In each of four experiments, two 12-cm segments of a rat small intestine were excised and washed once with isotonic phosphate buffer, pH 7.4. Segments from each animal were randomly assigned to control (not washed by EGTA) and experimental (washed by EGTA) groups. The use of paired segments from the same animal in the control and experimental groups reduced any differences among animals in the amounts of bound BAL in the intestine. The intestinal segments were ligated at each end and fastened to a catheter at one end, for injection or removal of solutions from the lumen.

Control segments were first injected with 1 ml of isotonic phosphate buffer, pH 7.5. To release the BAL bound the intestinal surfaces, experimental segments received the same isotonic buffer containing 1 mM EGTA. The intestinal segments were placed on a polystyrene weighing dish (14 cm$_2$) containing 5 ml of the same isotonic buffer and gently shaken for 30 minutes. The experimental segments were then washed once with isotonic phosphate-EGTA solution and twice with the isotonic buffer. The control intestine was washed three times with the isotonic buffer.

To allow uptake of cholesterol by the intestinal segments, a 1 ml aliquot containing 0.2 mM [$^3$H]-cholesterol oleate (Amersham, Arlington Heights, Ill.) and 6 mM taurocholate (Sigma Chemical Co., St. Louis, Mo.), a cofactor for BAL, was then placed in each intestine. After incubation for 60 minutes with gentle shaking in a polystyrene weighing dish, the contents in the intestinal segments were removed. The segments were washed three times with isotonic buffer.

To measure the uptake of radioactive cholesterol by the control and experimental intestinal segments, the central 10 cm of each intestinal segment was removed and further cut into four segments of about 2.5 cm, each of which was placed into scintillation vials containing 1 ml of 2% sodium dodecylsulfate plus 8M urea for the solubilization of the tissue. After the solubilization process, 10 ml of Hydrocount™ (J. T. Baker, Inc., Phillipsburg, N.J.) was added to each vial, and the amount of radioactivity from $^3$H-cholesterol in the intestinal segments was counted using a Beckman Scintillation Counter (Fullerton, Calif.).

Figure 3:
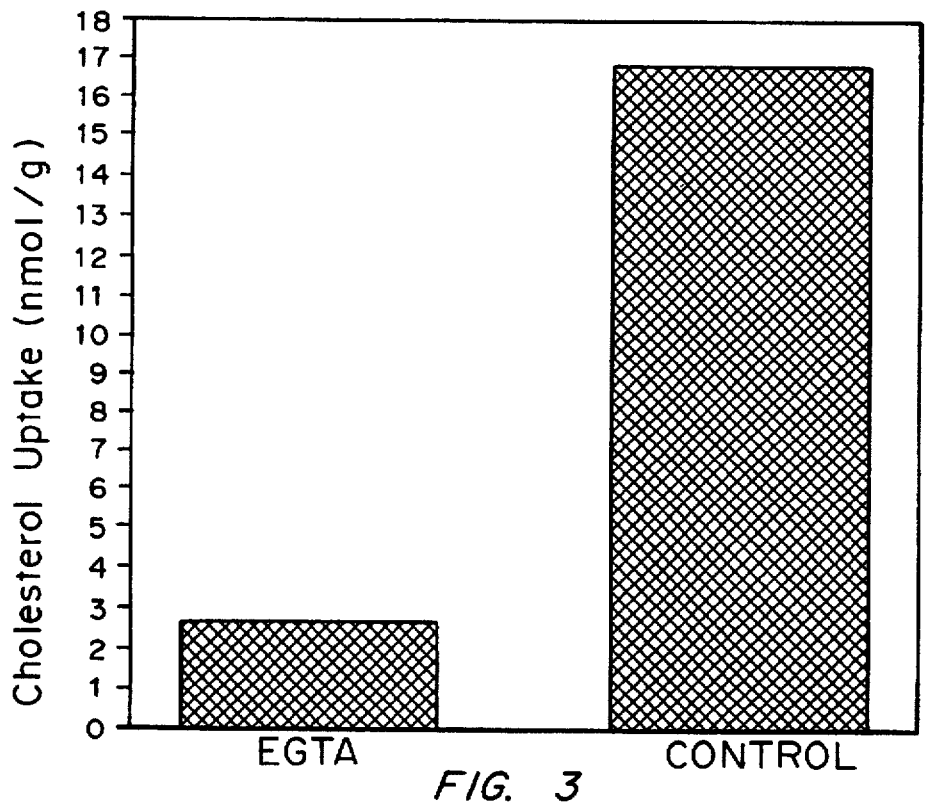
FIG. 3 shows the cholesterol uptake in nmol/g/h of radioactive cholesterol (oleate) ester in rat intestine either treated or untreated with Ethylene-bis(oxyethylenenitrilo)] tetraacetic acid (EGTA) to remove BAL.

The results from the four experiments are shown in Table V and FIG. 3.

TABLE V

Effect of Treatment with EGTA on the Cholesterol Uptake of Rat Intestine

| Experiment | EGTA Treatment nmol/g | Control | % of control |
|---|---|---|---|
| 1 | 1.41 | 11.65 | 12.10 |
| 2 | 4.25 | 20.40 | 20.83 |
| 3 | 2.85 | 12.78 | 22.30 |
| 4 | 2.23 | 22.28 | 10.01 |
| Average SD | 2.69 | 16.78 | 16.31 |
| | 1.20 | 5.34 | 6.16 |
| | P < .005 | | P < .0001 |

(EGTA = [Ethylene-bis(oxyethylenenitrilo)]tetraacetic acid.)

As shown in Table V, EGTA treatment reduced cholesterol uptake by intestinal epithelial cells to about 16% of the control uptake. The statistical significance of the raw data (p<0.005) and the data calculated as percent of control (p<0.0001) showed an extremely high confidence level of the difference. These results indicated that BAL, attached to intestinal surface, mediates the uptake of cholesterol from the intestinal lumen by the intestinal lining epithelial cells.

(c) In addition to the role of PAL in the uptake of cholesterol from cholesterol ester, it also mediate the direct uptake of free cholesterol Since about 85% of dietary cholesterol are in free cholesterol form, it is important to establish the role of BAL in the uptake of free cholesterol.

In vitro experiment was carried out to compare the uptake of radioactive cholesterol in control intestines as compared to the intestines from which the bound BAL has been removed by EGTA. Table VI shows the results from three experiments. The mean value of the control experiment was the uptake of 16.38 nmol/g intestine/h. The mean value for the EGTA treated intestine is 4.40 nmol/g intestine/h. The removal of PAL caused a reduction by about 70% of the free cholesterol uptake. In spite of the relatively large variations among three rats, the difference of the two groups is highly significant (p<0.005).

TABLE VI

Free cholesterol uptake by rat intestine (nmol/g/h)

| | EGTA treated | CONTROL | % OF CONTROL |
|---|---|---|---|
| EXP1 | 5.21 | 17.83 | 29.22 |
| EXP2 | 4.98 | 26.13 | 19.06 |
| EXP3 | 6.00 | 9.95 | 60.30 |

TABLE VI-continued

Free cholesterol uptake by rat intestine
(nmol/g/h)

| | EGTA treated | CONTROL | % OF CONTROL |
|---|---|---|---|
| EXP4 | 2.64 | 14.69 | 17.97 |
| EXP5 | 3.37 | 13.31 | 25.32 |
| MEAN | 4.44 | 16.38 | 30.37 |
| N | 5 | 5 | 5 |
| SE | 0.62 | 2.75 | 7.76 |

A two-fold concentrated cholesterol stock solution was prepared by emulsifying 6 μmol (specific activity=1.6 μCi/-μmol) of cholesterol and 0.6 μmol of dioleoylphosphatidylcholine in 15 ml of isotonic phosphate buffer, pH 7.4. The mixture was emulsified using a W-380 sonicator (Heat-System-Ultrasonics,Inc) at a setting of 5 (50% maximum output. for 30 s. in an ice bath.

After cooling, the mixture was further sonicated for an additional 30 sec.

Two segments of rat intestine (11 cm) each were washed once with isotonic phosphate buffer (pH 7.4) and the segments were ligated at both ends. One ml of the isotonic phosphate buffer with and without 1 mMEGTA was then injected into each intestine segment. The segment was placed on a polystyrene weighing dish (14 cm square) containing 5 ml of isotonic phosphate buffer. After incubation, the solution in the intestine were replaced with 1 ml of [$^3$H] cholesterol (0.2 mM) and 6 mM taurocholate and the segments were placed on the incubation tray on top of the ice bath as described above. The intestine segments were then washed 3 times with isotonic phosphate buffer and an 8 cm section of each intestine segment (about 0.7 g) was cut into 2 cm pieces and each piece placed in 1 ml of 2% SDS-8M urea for solubilization of the tissue. To this mixture, 10 ml of Hydracount™ was added for counting radioactivity as described in Example 3a.

(d) Heparin inhibits the uptake of free cholesterol by rat intestine

The uptake of [$^3$H] cholesterol oleate by rat intestine was studied in vitro in the presence of added heparin (10 mg/ml). The procedure was essentially the same as that described in Example 3d. Table VII shows that the control (column-1 presence of taurocholate and absence of heparin), the mean uptake is 20.65 nmol/g/h. In the presence of heparin (column 2) is 2.62 nmol/g/h. The difference is significant (p<0.05). The value from heparin inhibition is near that of the background uptake in the absence of taurocholate.

TABLE VII

EFFECT OF HEPARIN ON THE UPTAKE OF [$^3$H] CHOLESTEROL OLEATE BY RAT INTESTINE DATA IN nmol/g/h

| Experimental Group | 1 | 2 | 3 |
|---|---|---|---|
| [$^3$H]cholesterol oleate | + | + | + |
| Taurocholate | + | + | − |
| Heparin | − | + | − |
| EXP1 | 17.43 | 4.00 | 1.41 |
| EXP2 | 14.61 | 1.37 | 0.87 |
| EXP3 | 29.90 | 2.50 | 3.85 |
| AVERAGE = | 20.63 | 2.62 | 2.04 |
| N = | 3 | 3 | 3 |
| SD = | 8.14 | 1.32 | 1.59 |

The experimental procedure is the same as described in Example 3b. The intestine was washed with isotonic phosphate buffer without EGTA so the bound BAL was not removed from the intestine surface. Heparin (ICN Chemicals, Costa Mesa, Calif.) concentration in the uptake solution was 10 mg/ml.

(e) Addition of BAL to EGTA-treated/intestine restored cholesterol uptake

Materials and Reagents. Native human milk bile salt-activated lipase (N-BAL) was purified as described in Wang, C.-S., and K. Johnson, "Purification of human milk bile salt-activated lipase," Anal. Biochem. 133:457–461 (1983), incorporated herein by reference. The recombinant truncated form of BAL (T-BAL, residues 1–538 lacking the carboxy terminal end) was prepared as described in Example 1, and reported by Downs, D. et al. Biochemistry 33:7979–7985, (1994).

[1α-2α(n)-$^3$H] cholesterol oleate ($^3$H-cholesterol) was purchased from Amersham (Arlington Heights, Ill.). Other chemical reagents were purchased from Sigma Chemical Co, St. Louis, Mo.

A two-fold concentrated cholesterol oleate stock solution was prepared by emulsifying 6 μmol of $^3$H-cholesterol (1.6 μCi/μmol) and 0.6 μmol of dioleoyl-phosphatidylcholine 4 in 15 ml of isotonic sodium phosphate buffer, pH 7.4. The mixture was emulsified using a W-380 sonicator (Heat-system Ultrasonics, Inc., Farmingdale, N.Y.) at a setting of 5 (50% maximum output) for 30 seconds in an ice bath. After cooling, the mixture was further sonicated for an additional 30 seconds.

Methods

In each of five experiments, three segments of rat small intestine (11 cm each) were washed once with isotonic buffer (pH 7.4), and the segments were ligated at both ends, with a catheter inserted into one end of each intestine segment for injection of solutions. One ml of isotonic phosphate buffer containing 1 mM EGTA to release BAL attached to the intestinal surface, as demonstrated in Example 1(a), was then injected into each intestinal segment. The segments were placed on a polystyrene weighing dish (14 cm square) containing 5 ml of the isotonic phosphate buffer to maintain moisture and incubated with gentle shaking for 30 minutes on top of an ice bath. After incubation, the intestinal segments were washed once with the EGTA-containing isotonic buffer, and twice with isotonic buffer containing 0.2 mM calcium chloride. One of the segments was then injected with 1 ml of the purified N-BAL, and the second segment was injected with 1 ml of T-BAL, with the average enzyme concentration of 0.8 mg/ml, in isotonic phosphate buffer and in the presence of 0.2 mM Ca$^{+2}$. The third intestinal segment, to which no BAL was added, was the control. These intestinal segments were then placed on the incubation tray again and incubated with gentle shaking for 30 minutes. After incubation, the solutions in the segments were removed and replaced with 1 ml [$^3$H] cholesterol oleate (0.2 mM) and 6 mM taurocholate in isotonic buffer. After incubation with shaking, as described above, the segments were then washed three times with isotonic phosphate buffer, and an 8 cm segment of each intestinal segment (about 0.7 g) was cut into 2 cm pieces, each of which was placed in 1 ml of 2% SDS-8M urea for solubilization of the tissue. To this mixture, 10 ml of Hydrocount™ was added and radioactivity was counted as described in Example 1(b).

The results are shown in Table VIII.

TABLE VIII

Cholesterol Uptake (nmol/g/h) in the Presence of Recombinant tBAL.

| Exper. | Control | % of N-BAL* | +T-BAL | % of N-BAL* | +N-BAL | % |
|---|---|---|---|---|---|---|
| 1 | 5.28 | 64.86 | 4.61 | 56.63 | 8.14 | 100 |
| 2 | 4.24 | 38.23 | 6.43 | 57.98 | 11.09 | 100 |
| 3 | 5.52 | 44.12 | 9.78 | 78.18 | 12.51 | 100 |
| 4 | 4.91 | 57.49 | 4.34 | 50.82 | 8.54 | 100 |
| 5 | 13.85 | 43.62 | 11.42 | 35.97 | 31.75 | 100 |
| MEAN | 6.76 | 49.67 | 7.32 | 55.92 | 14.41 | 100 |
| SD | 3.99 | 11.07 | 3.16 | 15.20 | 9.86 | |
| SE | 1.79 | 4.95 | 1.41 | 6.80 | 4.41 | |

*N-BAL is native BAL purified from human milk; T-BAL is recombinant truncated BAL (without C-tail).

As shown in Table VIII, cholesterol uptake was compared in EGTA-washed intestinal segments without added BAL (control), EGTA-washed segments treated with truncated BAL (+T-BAL), and EGTA-washed segments treated with purified native human BAL (+N-BAL). Cholesterol uptake, measured in nmol cholesterol uptake/g intestine/hour, is shown in the left column of each group. The mean uptake values of the five experiments were Control 6.76, +T-BAL 7.32, and +BAL 14.41. The uptake in control segments represented non-specific trapping of radioactive cholesterol in intestinal segments caused, for example, by fusion of cholesterol micelles with intestinal cell membrane, and by residual intestinal BAL that remained after EGTA washing.

Because of the large deviation within each group due to biological differences among five rats, the data were calculated as percentage of +N-BAL group, and are presented in the right column of each group. The means of the percentage data show that uptake in Control was 49.67% and in +T-BAL was 55.92% of the +N-BAL group (100%). The difference between +N-BAL and +T-BAL uptake is statistically significant ($p<0.005$).

If the Control data are subtracted from that of the +T-BAL and that of the +N-BAL, the mean net uptakes are:

+T-BAL: 7.32−6.76=0.56 nmol/g/h

+N-BAL: 14.41−6.76=7.65 nmol/g/h

The net cholesterol uptake for +N-BAL is about fourteen times that for +T-BAL. The percentage difference of these two groups is also statistically highly significant ($p<0.005$).

These results demonstrate that: (a) the reduced cholesterol uptake by EGTA- or EDTA-treated intestine is mediated by BAL loss, not by damage of cholesterol uptake machinery; and (b) the restoration of cholesterol uptake is due to the binding of the BAL carboxy terminal tail, which was lacking in the T-BAL, to the intestinal surface.

EXAMPLE 4

Addition of C-tail to intestinal content releases bound endogenous BAL

Experiments were conducted to demonstrate that C-tail can compete for binding to intestinal surface CT-receptors resulting in the displacement of bound endogenous BAL.

(a) Preparation of C-tail

A procedure has been devised to prepare pure C-tail of BAL from BAL. It should be noted that the purification of C-tail is very effective, so the starting BAL need not be completely homogeneous. BAL used in these C-tail isolation experiments was enriched by Heparin-Sepharose™ column (bed volume 14×1.5 cm) chromatography as described previously (Wang and Johnson, *Anal. Bio.* 133:457–461, 1983).

Three hundred ml of human skim milk was first centrifuged at 20,000 rpm for 2 h. The supernatant was filtered and applied onto the Heparin-Sepharose™ column which had been preequilibrated with 50 mM Tris-HCl buffer at pH 8.0. After loading, the column was washed with 200 ml of the equilibrating buffer and the BAL was eluted with 0.3M NaCl in the equilibrating buffer and collected in 5 ml fractions. The fractions was assayed for the esterase activity of BAL using p-nitrophenyl acetate as substrate. The fractions containing the BAL activity was pooled and dialyzed against distilled water and lyophilized. The yield was about 100 to 150 mg of dried materials from each batch. For the C-tail purification, a pooling from three batches of the partially purified BAL (about 350 mg) was first treated with 8M urea (10 mg/ml) for 2 h at room temperature and dialyzed against 50 mM Tris-HCl overnight. The denatured BAL was digested with trypsin and chymotrypsin (substrate:protease ratio of 50:1, w/w) for 4 h at 37° C. The same amounts of trypsin and chymotrypsin were added to this mixture for the second time and the incubation continued overnight at 37° C. The digest was then dialyzed against distilled water and lyophilized. The dried powder was dissolved in 5 ml of 70% formic acid and 50 mg of cyanogen bromide, sealed in a glass tube, and incubated at room temperature for overnight. The solution was diluted 10 times with distilled water and lyophilized. The material was further dissolved with distilled water and dialyzed and the insoluble material was removed by centrifugation. The soluble fraction was then lyophilized. The dried material was then solubilized with 3 ml of 50 mM Tris-HCl buffer containing 0.15M NaCl for gel-permeation chromatography using FPLC (fast protein liquid chromatography) using a two-tandem linked Sepharose™ column. One ml of sample was applied on the column for each run of chromatography. Carbohydrate analysis of the eluent fractions (Dubois, et al. *Anal. Chem.* 28:350–356, 1956) indicated that the tail was eluted at fractions of 21–25 (1 ml/fraction).

b) Structure and composition of C-tail

N-terminal sequence and amino acid composition analyses of the material from the carbohydrate containing FPLC fractions indicated that the material corresponded to human BAL region containing residue of 528–712. As shown in Table IX, the amine acid composition of the purified C-tail and the composition based on the known sequence are very similar. From β-elimination experiment using alkali for the release of the O-linked oligosaccharide and in the further amine acid composition analysis of the sample, it was determined that between 8 to 10 residues of threonine were destroyed in each molecule of C-tail, while up to one residue of serine was destroyed by the same procedure. Therefore, it was concluded that most, if not all, of the oligosaccharides are attached to threonine residue in the C-tail.

TABLE IX

The amino acid composition of isolated of the C-tail of human milk BAL and after treatment with alkali(0.1 NNaOH).

| Amino Acid Residues | # residues (From known sequence) | # residues (Experimental) (Set Lysine = 1.0) | # residues (after β-elimination) |
|---|---|---|---|
| Lys | 1 | 1.0 | 1 |
| Asp | 18 | 17.8 | 20 |
| Thr | 23 | 22.4 | 14 |
| Ser | 15 | 13.5 | 14 |
| Glx | 6 | 6.1 | 8 |
| Pro | 60 | 56.9 | 60 |
| Gly | 26 | 25.6 | 28 |

TABLE IX-continued

The amino acid composition of isolated of the C-tail of human milk BAL and after treatment with alkali(0.1 NNaOH).

| Amino Acid Residues | # residues (From known sequence) | # residues (Experimental) (Set Lysine = 1.0) | # residues (after β-elimination) |
|---|---|---|---|
| Ala | 18 | 17.9 | 20 |
| Val | 17 | 16.8 | 18 |
| Leu | 1 | 1.3 | 2 |
| | | | Total = 185 |

Calculated peptide M.W.=17,014

Data from the further analysis of the carbohydrate composition of the C-tail of human milk BAL based on the gas-liquid chromatography of the alditol acetate derivative (Griggs et al. *Anal. Biochem.* 43:369–381, 1971) indicated the presence of fucose, galactose, galactosamine and glucosamine in the C-tail as shown in Table X. Since galactosamine is the anchoring sugar for linking carbohydrate to the polypeptide chain from the ratio of lysine and galactosamine, it was estimated that there are about 8 to 10 oligosaccharide per C-tail molecule.

TABLE X

Carbohydrate composition of C-tail of human milk BAL

| | μmol/mg | molar ratio |
|---|---|---|
| Fucose | 0.32 | 1.0 |
| Galactose | 0.95 | 3.0 |
| GlcNH$_2$ | 0.69 | 2.2 |
| GalNH$_2$ | 0.36 | 1.1 | c) C-tail causes the release of endogeneous BAL from rat intestine

Experiments were carried out to determine whether isolated C-tail domain of human milk BAL can displace bound BAL from rat intestine surface. In these experiments, different amounts of C-tail were placed in the solutions contained inside of the ligated rat intestines. The BAL activity which was released after 30 minutes was determined.

The incubation of BAL intestine with EGTA and BAL C-tail and the determination of the BAL lipolytic activity in the eluate were as described in Example 3a.

The data are shown in Table XI. The results indicated that isolated C-tail is effective in displacing the bound endogeneous BAL from rat intestine.

TABLE XI

Release of endogeneous BAL from Rat intestine by EGTA and various doses of purified C-tail.

| Isotonic buffer | EGTA | BAL C-tal (mg/ml) | | | | |
|---|---|---|---|---|---|---|
| | | 0.05 | 0.1 | 0.2 | 0.5 | 1.0 |
| | | Eluted BAL activity μmol/g intestine/h) | | | | |
| 13.00 | 253.20 | 107.80 | 30.00 | 149.30 | 96.00 | 65.80 |
| 6.60 | 189.80 | 82.00 | 35.40 | 120.50 | 99.30 | 97.80 |
| 6.90 | 169.60 | 131.10 | 97.50 | 190.10 | 379.00 | 274.10 |
| 10.50 | 153.50 | 33.50 | 194.50 | 33.60 | 47.00 | 190.30 |
| 6.80 | 105.50 | 95.00 | 60.00 | 245.30 | 269.00 | 193.71 |
| 5.50 | 133.49 | 41.37 | 362.81 | 288.80 | 47.95 | 43.12 |

TABLE XI-continued

Release of endogeneous BAL from Rat intestine by EGTA and various doses of purified C-tail.

| | Isotonic buffer | EGTA | BAL C-tal (mg/ml) | | | | |
|---|---|---|---|---|---|---|---|
| | | | 0.05 | 0.1 | 0.2 | 0.5 | 1.0 |
| | | | Eluted BAL activity μmol/g intestine/h) | | | | |
| Mean | 8.82 | 167.22 | 81.80 | 130.04 | 171.27 | 156.38 | 144.14 |
| SE | 1.18 | 20.85 | 15.54 | 52.68 | 37.27 | 55.64 | 36.50 |

EXAMPLE 5

Competitive Inhibition of Cholesterol Uptake by the C-Tail of BAL

The foregoing examples demonstrates that C-tail can elute the endogenously bound BAL from the rat intestinal surface. The following study demonstrates that the isolated C-tail can competitively inhibit cholesterol uptake in the isolated rat intestine.

In the current study, three intestine segments were washed with isotonic phosphate buffer, pH 7.4. One of the intestine segment was incubated with the substrate [$^3$H] cholesterol oleate (0.2 mM) alone as control. The control intestine segment should have a higher rate of cholesterol uptake because the endogenous BAL on the intestinal surface is available for the transport of cholesterol. The second intestine segment was incubated with the same [$^3$H] cholesterol oleate and EGTA (1 mM). EGTA is known to elute endogenous BAL from the intestinal surface. The third intestine segment was incubated with the same [$^3$H] cholesterol oleate and the isolated C-tail (0.2 mg/ml).

Figure 4:
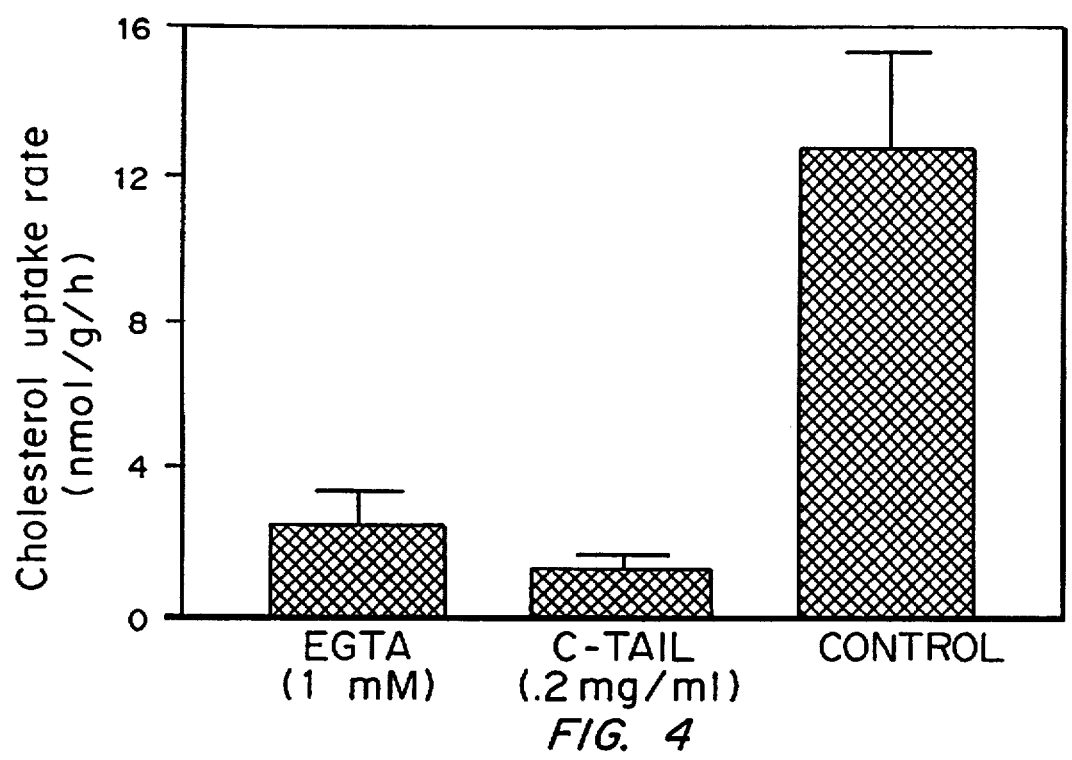
FIG. 4 is a graph showing the cholesterol uptake rate (nmol/g/h) for 1 mM EGTA, 0.2 mg/ml C-tal, and the control in rat intestine.

The data shown in the enclosed Table XII are from 4 separate experiments. The averaged data are shown in FIG. 4. These results indicate that when C-tail is present, the cholesterol uptake is only about 10% of that of the control intestine. This compares favorably with the uptake of cholesterol when EGTA is present, which is about 18% of the control. These results demonstrate that the C-tail can effectively compete with the endogenous bound BAL for intestinal surface binding. The inhibition is due to the replacement of endogenous BAL on the intestinal surface by C tail, indicating that C-tail can be used to reduce the cholesterol uptake from human diet.

TABLE XII

Reduction in Cholesterol Uptake.

| Final Conc. | EGTA (1 mM) | C-Tail (0.2 mg/ml) | Control |
|---|---|---|---|
| | 4.80 | 0.99 | 15.70 |
| | 0.34 | 1.17 | 17.80 |
| | 2.25 | 0.55 | 11.28 |
| | 2.20 | 2.30 | 6.43 |
| Average | 2.40 | 1.25 | 12.80 |
| SD | 1.83 | 0.75 | 5.04 |
| SE | 0.92 | 0.37 | 2.52 |

Modifications and variations of the present invention will be obvious to those skilled in the art from the foregoing detailed description of the invention. Such modifications and variations are intended to come within the scope of the appended claims.

We claim:

1. A method for reducing intestinal absorption of cholesterol in a human comprising orally administering to an individual in need of treatment thereof a polypeptide comprising at least four eleven amino acid repeats having at least three prolines present in the carboxy terminal region of human bile salt-activated lipase as shown in Sequence ID No. 1, wherein the polypeptide cannot hydrolyze cholesterol ester and is administered in an amount effective to reduce cholesterol uptake into the intestinal endothelium cells.

2. The method of claim 1 wherein the polypeptide consists of at least four eleven amino acid repeats present in amino acid residues 539–722 of Sequence ID No. 1 and binds to intestinal endothelium cells.

3. The method of claim 1 wherein the polypeptide comprises the region of bile salt-activated lipase containing the catalytic site which has been inactivated.

4. The method of claim 1 wherein the polypeptide comprises the region of bile salt-activated lipase wherein the heparin binding site is unable to bind to heparin.

5. The method of claim 1 wherein the polypeptide is in combination with a pharmaceutical carrier acceptable for oral administration.

6. The method of claim 5 further comprising orally administering the polypeptide in an amount effective to lower the blood cholesterol levels as compared with levels prior to administration of the carboxy terminal region.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 722 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: internal ( x i ) SEQUENCE DESCRIPTION: SEQ ID NO:1:

```
Ala  Lys  Leu  Gly  Ala  Val  Tyr  Thr  Glu  Gly  Gly  Phe  Val  Glu  Gly  Val
 1              5                  10                          15

Asn  Lys  Lys  Leu  Gly  Leu  Leu  Gly  Asp  Ser  Val  Asp  Ile  Phe  Lys  Gly
                20                  25                          30

Ile  Pro  Phe  Ala  Ala  Pro  Thr  Lys  Ala  Leu  Glu  Asn  Pro  Gln  Pro  His
                35                  40                          45

Pro  Gly  Trp  Gln  Gly  Thr  Leu  Lys  Ala  Lys  Asn  Phe  Lys  Lys  Arg  Cys
      50                      55                      60

Leu  Gln  Ala  Thr  Ile  Thr  Gln  Asp  Ser  Thr  Tyr  Gly  Asp  Glu  Asp  Cys
65                       70                      75                          80

Leu  Tyr  Leu  Asn  Ile  Trp  Val  Pro  Gln  Gly  Arg  Lys  Gln  Val  Ser  Arg
                85                  90                          95

Asp  Leu  Pro  Val  Met  Ile  Trp  Ile  Tyr  Gly  Gly  Ala  Phe  Leu  Met  Gly
                100                 105                         110

Ser  Gly  His  Gly  Ala  Asn  Phe  Leu  Asn  Asn  Tyr  Leu  Tyr  Asp  Gly  Glu
                115                 120                         125

Glu  Ile  Ala  Thr  Arg  Gly  Asn  Val  Ile  Val  Val  Thr  Phe  Asn  Tyr  Arg
      130                     135                     140

Val  Gly  Pro  Leu  Gly  Phe  Leu  Ser  Thr  Gly  Asp  Ala  Asn  Leu  Pro  Gly
145                      150                     155                         160

Asn  Tyr  Gly  Leu  Arg  Asp  Gln  His  Met  Ala  Ile  Ala  Trp  Val  Lys  Arg
                165                 170                         175

Asn  Ile  Ala  Ala  Phe  Gly  Gly  Asp  Pro  Asn  Asn  Ile  Thr  Leu  Phe  Gly
                180                 185                         190

Glu  Ser  Ala  Gly  Gly  Ala  Ser  Val  Ser  Leu  Gln  Thr  Leu  Ser  Pro  Tyr
      195                     200                     205

Asn  Lys  Gly  Leu  Ile  Arg  Arg  Ala  Ile  Ser  Gln  Ser  Gly  Val  Ala  Leu
      210                     215                     220

Ser  Pro  Trp  Val  Ile  Gln  Lys  Asn  Pro  Leu  Phe  Trp  Ala  Lys  Lys  Val
225                      230                     235                         240

Ala  Glu  Lys  Val  Gly  Cys  Pro  Val  Gly  Asp  Ala  Ala  Arg  Met  Ala  Gln
                245                 250                         255

Cys  Leu  Lys  Val  Thr  Asp  Pro  Arg  Ala  Leu  Thr  Leu  Ala  Tyr  Lys  Val
                260                 265                         270

Pro  Leu  Ala  Gly  Leu  Glu  Tyr  Pro  Met  Leu  His  Tyr  Val  Gly  Phe  Val
                275                 280                         285

Pro  Val  Ile  Asp  Gly  Asp  Phe  Ile  Pro  Ala  Asp  Pro  Ile  Asn  Leu  Tyr
                290                 295                         300
```

```
Ala  Asn  Ala  Ala  Asp  Ile  Asp  Tyr  Ile  Ala  Gly  Thr  Asn  Asn  Met  Asp
305                      310                     315                          320

Gly  His  Ile  Phe  Ala  Ser  Ile  Asp  Met  Pro  Ala  Ile  Asn  Lys  Gly  Asn
                    325                      330                         335

Lys  Lys  Val  Thr  Glu  Glu  Asp  Phe  Tyr  Lys  Leu  Val  Ser  Glu  Phe  Thr
               340                      345                    350

Ile  Thr  Lys  Gly  Leu  Arg  Gly  Ala  Lys  Thr  Thr  Phe  Asp  Val  Tyr  Thr
          355                     360                    365

Glu  Ser  Trp  Ala  Gln  Asp  Pro  Ser  Gln  Glu  Asn  Lys  Lys  Lys  Thr  Val
     370                    375                    380

Val  Asp  Phe  Glu  Thr  Asp  Val  Leu  Phe  Leu  Val  Pro  Thr  Glu  Ile  Ala
385                      390                    395                          400

Leu  Ala  Gln  His  Arg  Ala  Asn  Ala  Lys  Ser  Ala  Lys  Thr  Tyr  Ala  Tyr
                    405                     410                         415

Leu  Phe  Ser  His  Pro  Ser  Arg  Met  Pro  Val  Tyr  Pro  Lys  Trp  Val  Gly
               420                      425                    430

Ala  Asp  His  Ala  Asp  Asp  Ile  Gln  Tyr  Val  Phe  Gly  Lys  Pro  Phe  Ala
          435                     440                    445

Thr  Pro  Thr  Gly  Tyr  Arg  Pro  Gln  Asp  Arg  Thr  Val  Ser  Lys  Ala  Met
     450                    455                    460

Ile  Ala  Tyr  Trp  Thr  Asn  Phe  Ala  Lys  Thr  Gly  Asp  Pro  Asn  Met  Gly
465                      470                     475                         480

Asp  Ser  Ala  Val  Pro  Thr  His  Trp  Glu  Pro  Tyr  Thr  Thr  Glu  Asn  Ser
               485                      490                         495

Gly  Tyr  Leu  Glu  Ile  Thr  Lys  Lys  Met  Gly  Ser  Ser  Ser  Met  Lys  Arg
               500                     505                    510

Ser  Leu  Arg  Thr  Asn  Phe  Leu  Arg  Tyr  Trp  Thr  Leu  Thr  Tyr  Leu  Ala
          515                     520                    525

Leu  Pro  Thr  Val  Thr  Asp  Gln  Glu  Ala  Thr  Pro  Val  Pro  Pro  Thr  Gly
     530                    535                    540

Asp  Ser  Glu  Ala  Thr  Pro  Val  Pro  Pro  Thr  Gly  Asp  Ser  Glu  Thr  Ala
545                      550                    555                          560

Pro  Val  Pro  Pro  Thr  Gly  Asp  Ser  Gly  Ala  Pro  Pro  Val  Pro  Pro  Thr
                    565                    570                         575

Gly  Asp  Ser  Gly  Ala  Pro  Pro  Val  Pro  Pro  Thr  Gly  Asp  Ser  Gly  Ala
               580                    585                     590

Pro  Pro  Val  Pro  Pro  Thr  Gly  Asp  Ser  Gly  Ala  Pro  Pro  Val  Pro  Pro
          595                    600                     605

Thr  Gly  Asp  Ser  Gly  Ala  Pro  Pro  Val  Pro  Pro  Thr  Gly  Asp  Ser  Gly
     610                    615                     620

Ala  Pro  Pro  Val  Pro  Pro  Thr  Gly  Asp  Ser  Gly  Ala  Pro  Pro  Val  Pro
625                    630                     635                          640

Pro  Thr  Gly  Asp  Ala  Gly  Pro  Pro  Val  Pro  Pro  Thr  Gly  Asp  Ser
                    645                    650                     655

Gly  Ala  Pro  Pro  Val  Pro  Pro  Thr  Gly  Asp  Ser  Gly  Ala  Pro  Pro  Val
               660                    665                          670

Thr  Pro  Thr  Gly  Asp  Ser  Glu  Thr  Ala  Pro  Val  Pro  Pro  Thr  Gly  Asp
          675                    680                     685

Ser  Gly  Ala  Pro  Pro  Val  Pro  Pro  Thr  Gly  Asp  Ser  Glu  Ala  Ala  Pro
     690                    695                     700

Val  Pro  Pro  Thr  Asp  Asp  Ser  Lys  Glu  Ala  Gln  Met  Pro  Ala  Val  Ile
705                    710                     715                          720

Arg  Phe
```

( 2 ) INFORMATION FOR SEQ ID NO:2:

( i ) SEQUENCE CHARACTERISTICS:
        ( A ) LENGTH: 742 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: internal ( i x ) FEATURE:
        ( A ) NAME/KEY: Modified-site
        ( B ) LOCATION: 186..187
        ( D ) OTHER INFORMATION: /note="Position 187 represents a
            potential N- linked glycosylation site."

( i x ) FEATURE:
        ( A ) NAME/KEY: Modified-site
        ( B ) LOCATION: 193..194
        ( D ) OTHER INFORMATION: /note="The serine at position 194
            represents an active site serine."

( i x ) FEATURE:
        ( A ) NAME/KEY: misc. feature
        ( B ) LOCATION: 1..742
        ( D ) OTHER INFORMATION: /Function ="Amino acid sequence for
            the Human Milk Bile Salt-activated Lipase."

( x i ) SEQUENCE DESCRIPTION: SEQ ID NO:2:

```
Met Gly Arg Leu Gln Leu Val Val Leu Gly Leu Thr Cys Cys Trp Ala
 1               5                  10                  15

Val Ala Ser Ala Ala Lys Leu Gly Ala Val Tyr Thr Glu Gly Gly Phe
            20                  25                  30

Val Glu Gly Val Asn Lys Lys Leu Gly Leu Leu Gly Asp Ser Val Asp
        35                  40                  45

Ile Phe Lys Gly Ile Pro Phe Ala Ala Pro Thr Lys Ala Leu Glu Asn
 50                  55                  60

Pro Gln Pro His Pro Gly Trp Gln Gly Thr Leu Lys Ala Lys Asn Phe
 65                  70                  75                  80

Lys Lys Arg Cys Leu Gln Ala Thr Ile Thr Gln Asp Ser Thr Tyr Gly
            85                  90                  95

Asp Glu Asp Cys Leu Tyr Leu Asn Ile Trp Val Pro Gln Gly Arg Lys
           100                 105                 110

Gln Val Ser Arg Asp Leu Pro Val Met Ile Trp Ile Tyr Gly Gly Ala
           115                 120                 125

Phe Leu Met Gly Ser Gly His Gly Ala Asn Phe Leu Asn Asn Tyr Leu
       130                 135                 140

Tyr Asp Gly Glu Glu Ile Ala Thr Arg Gly Asn Val Ile Val Val Thr
145                 150                 155                 160

Phe Asn Tyr Arg Val Gly Pro Leu Gly Phe Leu Ser Thr Gly Asp Ala
               165                 170                 175

Asn Leu Pro Gly Asn Tyr Gly Leu Arg Asp Gln His Met Ala Ile Ala
           180                 185                 190

Trp Val Lys Arg Asn Ile Ala Ala Phe Gly Gly Asp Pro Asn Asn Ile
       195                 200                 205

Thr Leu Phe Gly Glu Ser Ala Gly Gly Ala Ser Val Ser Leu Gln Thr
   210                 215                 220

Leu Ser Pro Tyr Asn Lys Gly Leu Ile Arg Arg Ala Ile Ser Gln Ser
225                 230                 235                 240

Gly Val Ala Leu Ser Pro Trp Val Ile Gln Lys Asn Pro Leu Phe Trp
```

```
                            245                          250                          255
    Ala Lys Lys Val Ala Glu Lys Val Gly Cys Pro Val Gly Asp Ala Ala
                    260                      265                      270
    Arg Met Ala Gln Cys Leu Lys Val Thr Asp Pro Arg Ala Leu Thr Leu
                    275                      280                      285
    Ala Tyr Lys Val Pro Leu Ala Gly Leu Glu Tyr Pro Met Leu His Tyr
            290                      295                      300
    Val Gly Phe Val Pro Val Ile Asp Gly Asp Phe Ile Pro Ala Asp Pro
    305                      310                      315                      320
    Ile Asn Leu Tyr Ala Asn Ala Ala Asp Ile Asp Tyr Ile Ala Gly Thr
                        325                      330                      335
    Asn Asn Met Asp Gly His Ile Phe Ala Ser Ile Asp Met Pro Ala Ile
                    340                      345                      350
    Asn Lys Gly Asn Lys Lys Val Thr Glu Glu Asp Phe Tyr Lys Leu Val
                355                      360                      365
    Ser Glu Phe Thr Ile Thr Lys Gly Leu Arg Gly Ala Lys Thr Thr Phe
            370                      375                      380
    Asp Val Tyr Thr Glu Ser Trp Ala Gln Asp Pro Ser Gln Glu Asn Lys
    385                      390                      395                      400
    Lys Lys Thr Val Val Asp Phe Glu Thr Asp Val Leu Phe Leu Val Pro
                        405                      410                      415
    Thr Glu Ile Ala Leu Ala Gln His Arg Ala Asn Ala Lys Ser Ala Lys
                    420                      425                      430
    Thr Tyr Ala Tyr Leu Phe Ser His Pro Ser Arg Met Pro Val Tyr Pro
                435                      440                      445
    Lys Trp Val Gly Ala Asp His Ala Asp Asp Ile Gln Tyr Val Phe Gly
        450                      455                      460
    Lys Pro Phe Ala Thr Pro Thr Gly Tyr Arg Pro Gln Asp Arg Thr Val
    465                      470                      475                      480
    Ser Lys Ala Met Ile Ala Tyr Trp Thr Asn Phe Ala Lys Thr Gly Asp
                        485                      490                      495
    Pro Asn Met Gly Asp Ser Ala Val Pro Thr His Trp Glu Pro Tyr Thr
                    500                      505                      510
    Thr Glu Asn Ser Gly Tyr Leu Glu Ile Thr Lys Lys Met Gly Ser Ser
                515                      520                      525
    Ser Met Lys Arg Ser Leu Arg Thr Asn Phe Leu Arg Tyr Trp Thr Leu
            530                      535                      540
    Thr Tyr Leu Ala Leu Pro Thr Val Thr Asp Gln Glu Ala Thr Pro Val
    545                      550                      555                      560
    Pro Pro Thr Gly Asp Ser Glu Ala Thr Pro Val Pro Pro Thr Gly Asp
                        565                      570                      575
    Ser Glu Thr Ala Pro Val Pro Pro Thr Gly Asp Ser Gly Ala Pro Pro
                    580                      585                      590
    Val Pro Pro Thr Gly Asp Ser Gly Ala Pro Pro Val Pro Pro Thr Gly
                595                      600                      605
    Asp Ser Gly Ala Pro Pro Val Pro Pro Thr Gly Asp Ser Gly Ala Pro
            610                      615                      620
    Pro Val Pro Pro Thr Gly Asp Ser Gly Ala Pro Pro Val Pro Pro Thr
    625                      630                      635                      640
    Gly Asp Ser Gly Ala Pro Pro Val Pro Pro Thr Gly Asp Ser Gly Ala
                        645                      650                      655
    Pro Pro Val Pro Pro Thr Gly Asp Ala Gly Pro Pro Val Pro Pro
                    660                      665                      670
```

| | | | | | | | | | | | | | | |
|---|---|---|---|---|---|---|---|---|---|---|---|---|---|---|
| Thr | Gly | Asp<br>675 | Ser | Gly | Ala | Pro | Pro<br>680 | Val | Pro | Pro | Thr | Gly<br>685 | Asp | Ser | Gly |
| Ala | Pro<br>690 | Pro | Val | Thr | Pro | Thr<br>695 | Gly | Asp | Ser | Glu | Thr<br>700 | Ala | Pro | Val | Pro |
| Pro<br>705 | Thr | Gly | Asp | Ser | Gly<br>710 | Ala | Pro | Pro | Val | Pro<br>715 | Pro | Thr | Gly | Asp | Ser<br>720 |
| Glu | Ala | Ala | Pro | Val<br>725 | Pro | Pro | Thr | Asp | Asp<br>730 | Ser | Lys | Glu | Ala | Gln<br>735 | Met |
| Pro | Ala | Val | Ile<br>740 | Arg | Phe | | | | | | | | | | |

( 2 ) INFORMATION FOR SEQ ID NO:3:

( i ) SEQUENCE CHARACTERISTICS:
        ( A ) LENGTH: 3018 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc. feature
        ( B ) LOCATION: 1..742
        ( D ) OTHER INFORMATION: /Function ="Nucleotides 679 through
            2904 encode the amino acid sequence for the Human Milk
            Bile Salt- activated Lipase."

( x i ) SEQUENCE DESCRIPTION: SEQ ID NO:3:

```
CTCAATTGGA GGATCAAAGT TGAGAAAAGT AATATTCGAC ATTTTTCGAT TCAACGGAGT        60
GGCCACCAAG ACGATGTCAT AGAAGTCTGA ACGAGTCTCA GTTCCAATTT GGTAGACCAC       120
TTCATACATC TTTGTTGGAT TTCCTGTGTA CTTGGTCTTT GTTTCTCCT  CGATGTACAT       180
TACTGAGCCA GATATAAGAT TGCTTTTGGA TGCCTGCAGA AGCCCTGAGC AAACAAGTTT       240
ATTGCCACCT TCTACTGCCC AAAGGCCAGA ATCAGAACAG GACAGTGACA CCGCCCCCAC       300
AAAGGCATTG ATGTCCGTGC TTTGGCCATA ATTGACCCTC ATAACAGGAG CAATCATTTC       360
ATTGAGGAAC TTCTCAGAAA AGCCGGCCTT TTGCAAGGTT TCAAGAAGTG TTCGATTAAG       420
CATTCCAAGG AAGTCATCTC CTCCTAGAGC ATGAAGTAAT TTTTCGACAC TACTGAAGGC       480
ATAGTCATGA GACTGGTAGC GGTAGATCCT CATGAACTTG TCTAACACGT CCTCTACCCA       540
CATGTGCATA CGGAGGGATT GAAATCCATA GCGCCAAACT AATTTAATCA CGTTAATTAT       600
GAACCAGTTG CTCTCCTCAA ATACCAGAGT CTCTCCATTA TATATCCCCA GTAGGCCACC       660
CAGAGGCTGA TGCTCACCAT GGGGCGCCTG CAACTGGTTG TGTTGGGCCT CACCTGCTGC       720
TGGGCAGTGG CGAGTGCCGC GAAGCTGGGC GCCGTGTACA CAGAAGGTGG GTTCGTGGAA       780
GGCGTCAATA AGAAGCTCGG CCTCCTGGGT GACTCTGTGG ACATCTTCAA GGGCATCCCC       840
TTCGCAGCTC CCACCAAGGC CCTGGAAAAT CCTCAGCCAC ATCCTGGCTG GCAAGGGACC       900
CTGAAGGCCA AGAACTTCAA GAAGAGATGC CTGCAGGCCA CCATCACCCA GGACAGCACC       960
TACGGGGATG AAGACTGCCT GTACCTCAAC ATTTGGGTGC CCCAGGGCAG GAAGCAAGTC      1020
TCCCGGGACC TGCCCGTTAT GATCTGGATC TATGGAGGCG CCTTCCTCAT GGGGTCCGGC      1080
CATGGGGCCA ACTTCCTCAA CAACTACCTG TATGACGGCG AGGAGATCGC CACACGCGGA      1140
AACGTCATCG TGGTCACCTT CAACTACCGT GTCGGCCCCC TTGGGTTCCT CAGCACTGGG      1200
GACGCCAATC TGCCAGGTAA CTATGGTCTT CGGGATCAGC ACATGGCCAT TGCTTGGGTG      1260
```

-continued

```
AAGAGGAATA TCGCGGCCTT CGGGGGGGAC CCCAACAACA TCACGCTCTT CGGGGAGTCT    1320
GCTGGAGGTG CCAGCGTCTC TCTGCAGACC CTCTCCCCCT ACAACAAGGG CCTCATCCGG    1380
CGAGCCATCA GCCAGAGCGG CGTGGCCCTG AGTCCTGGG TCATCCAGAA AAACCCACTC    1440
TTCTGGGCCA AAAGGTGGC TGAGAAGGTG GGTTGCCCTG TGGGTGATGC CGCCAGGATG    1500
GCCCAGTGTC TGAAGGTTAC TGATCCCCGA GCCCTGACGC TGGCCTATAA GGTGCCGCTG    1560
GCAGGCCTGG AGTACCCCAT GCTGCACTAT GTGGGCTTCG TCCCTGTCAT TGATGGAGAC    1620
TTCATCCCCG CTGACCCGAT CAACCTGTAC GCCAACGCCG CCGACATCGA CTATATAGCA    1680
GGCACCAACA ACATGGACGG CCACATCTTC GCCAGCATCG ACATGCCTGC CATCAACAAG    1740
GGCAACAAGA AACTCACGGA GGAGGACTTC TACAAGCTGG TCAGTGAGTT CACAATCACC    1800
AAGGGGCTCA GAGGCGCCAA GACGACCTTT GATGTCTACA CCGAGTCCTG GGCCCAGGAC    1860
CCATCCCAGG AGAATAAGAA GAAGACTGTG GTGGACTTTG AGACCGATGT CCTCTTCCTG    1920
GTGCCCACCG AGATTGCCCT AGCCCAGCAC AGAGCCAATG CCAAGAGTGC CAAGACCTAC    1980
GCCTACCTGT TTTCCCATCC CTCTCGGATG CCCGTCTACC CCAAATGGGT GGGGGCCGAC    2040
CATGCAGATG ACATTCAGTA CGTTTTCGGG AAGCCCTTCG CCACCCCCAC GGGCTACCGG    2100
CCCCAAGACA GGACAGTCTC TAAGGCCATG ATCGCCTACT GGACCAACTT TGCCAAAACA    2160
GGGGACCCCA ACATGGGCGA CTCGGCTGTG CCCACACACT GGGAACCCTA CACTACGGAA    2220
AACAGCGGCT ACCTGGAGAT CACCAAGAAG ATGGGCAGCA GCTCCATGAA GCGGAGCCTG    2280
AGAACCAACT TCCTGCGCTA CTGGACCCTC ACCTATCTGG CGCTGCCCAC AGTGACCGAC    2340
CAGGAGGCCA CCCCTGTGCC CCCCACAGGG GACTCCGAGG CCACTCCCGT GCCCCCCACG    2400
GGTGACTCCG AGACCGCCCC CGTGCCGCCC ACGGGTGACT CCGGGGCCCC CCCCGTGCCG    2460
CCCACGGGTG ACTCCGGGGC CCCCCCCGTG CCGCCCACGG GTGACTCCGG GGCCCCCCCC    2520
GTGCCGCCCA CGGGTGACTC CGGGGCCCCC CCCGTGCCGC CACGGGTGA CTCCGGGGCC    2580
CCCCCCGTGC CGCCCACGGG TGACTCCGGG GCCCCCCCCG TGCCGCCCAC GGGTGACTCC    2640
GGCGCCCCCC CCGTGCCGCC CACGGGTGAC GCCGGGCCCC CCCCGTGCC GCCCACGGGT    2700
GACTCCGGCG CCCCCCCCGT GCCGCCCACG GGTGACTCCG GGGCCCCCCC CGTGACCCCC    2760
ACGGGTGACT CCGAGACCGC CCCCGTGCCG CCCACGGGTG ACTCCGGGGC CCCCCCTGTG    2820
CCCCCCACGG GTGACTCTGA GGCTGCCCCT GTGCCCCCCA CAGATGACTC CAAGGAAGCT    2880
CAGATGCCTG CAGTCATTAG GTTTTAGCGT CCCATGAGCC TTGGTATCAA GAGGCCACAA    2940
GAGTGGGACC CCAGGGGCTC CCCTCCCATC TTGAGCTCTT CCTGAATAAA GCCTCATACC    3000
CCTGAAAAAA AAAAAAA                                                   3018
```

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( i x ) FEATURE:
        ( A ) NAME/KEY: misc. feature
        ( B ) LOCATION: 1..21
        ( D ) OTHER INFORMATION: /Function ="Primer."

(x i) SEQUENCE DESCRIPTION: SEQ ID NO:4:

CATATGGCGA AGCTGGGCGC C    21

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: NO (i x) FEATURE:
        (A) NAME/KEY: misc. feature
        (B) LOCATION: 1..24
        (D) OTHER INFORMATION: /Function ="Primer."

(x i) SEQUENCE DESCRIPTION: SEQ ID NO:5:

GGATCCTTAG GTGGCCTCCT GGTCG    25

(2) INFORMATION FOR SEQ ID NO:6:

(i) SEQUENCE CHARACTERISTICS:
        (A) LENGTH: 11 amino acids
        (B) TYPE: amino acid
        (D) TOPOLOGY: linear (i i) MOLECULE TYPE: protein (i i i) HYPOTHETICAL: NO (v) FRAGMENT TYPE: internal (i x) FEATURE:
        (A) NAME/KEY: misc. feature
        (B) LOCATION: 1..11
        (D) OTHER INFORMATION: /Function ="Concensus Sequence."

(x i) SEQUENCE DESCRIPTION: SEQ ID NO:6:

Pro Val Pro Pro Thr Gly Asp Ser Gly Ala Pro
          5                 10